United States Patent
Cocaign et al.

(10) Patent No.: US 10,357,314 B2
(45) Date of Patent: Jul. 23, 2019

(54) INSTRUMENTATION AND METHOD FOR REPAIR OF A BONE FRACTURE

(71) Applicant: Stryker European Holdings I, LLC, Kalamazoo, MI (US)

(72) Inventors: Mael Cocaign, La Riche (FR); Julien Borgnard, Goven (FR); Franck Day, Saint Médard sur Ille (FR); Yogesh Pathapati, Basel (CH); Oliver Ammann, Bern (CH); Philippe Lehmann, Lamboing (CH); Salman Chegini, Bern (CH)

(73) Assignee: Stryker European Holdings I, LLC, Kalamazoo, MI (US)

( * ) Notice: Subject to any disclaimer, the term of this patent is extended or adjusted under 35 U.S.C. 154(b) by 566 days.

(21) Appl. No.: 14/794,406

(22) Filed: Jul. 8, 2015

(65) Prior Publication Data

US 2017/0007307 A1     Jan. 12, 2017

(51) Int. Cl.
| | | |
|---|---|---|
| *A61B 17/88* | (2006.01) | |
| *A61B 19/00* | (2006.01) | |
| *A61B 17/17* | (2006.01) | |
| *A61B 90/00* | (2016.01) | |
| *A61B 17/00* | (2006.01) | |

(52) U.S. Cl.
CPC .......... *A61B 19/46* (2013.01); *A61B 17/1775* (2016.11); *A61B 90/06* (2016.02); *A61B 90/39* (2016.02); *A61B 2017/0046* (2013.01); *A61B 2017/0092* (2013.01); *A61B 2090/061* (2016.02); *A61B 2090/3966* (2016.02)

(58) Field of Classification Search
CPC ... A61B 90/06; A61B 2090/061; A61B 17/88; A61B 17/8872
See application file for complete search history.

(56) References Cited

U.S. PATENT DOCUMENTS

| | | | | | |
|---|---|---|---|---|---|
| 4,311,201 | A | * | 1/1982 | Stewart | ................... E21B 25/16 175/44 |
| 5,163,940 | A | * | 11/1992 | Bourque | ............ A61B 17/1714 606/103 |
| 5,334,192 | A | | 8/1994 | Behrens | |

(Continued)

OTHER PUBLICATIONS

Kelly et al., "Intramedullary Screw Fixation of Jones Fractures", Foot and Ankle International, vol. 22, No. 7, pp. 585-589, Jul. 2001.

(Continued)

*Primary Examiner* — Anu Ramana
(74) *Attorney, Agent, or Firm* — Lerner, David, Littenberg, Krumholz & Mentlik, LLP

(57) ABSTRACT

A device for assisting in the positioning and sizing of an implant includes an elongate member and a block. The elongate member has length indicia at axial locations along a length for measuring a first distance from a predetermined datum of the elongate member. The block is attached to and movable along the elongate member. The block includes width indicia for measuring a second distance in a direction transverse to the first distance. A method for assisting in the positioning and sizing of an implant includes moving the elongate member along the block to axial locations along such member to determine an appropriate width and depth of insertion of the implant.

25 Claims, 16 Drawing Sheets

(56) References Cited

U.S. PATENT DOCUMENTS

| | | | |
|---|---|---|---|
| 5,336,225 A | 8/1994 | Zang | |
| 5,354,300 A | 10/1994 | Goble et al. | |
| 5,443,509 A | 8/1995 | Boucher et al. | |
| 5,478,343 A | 12/1995 | Ritter | |
| 5,601,550 A | 2/1997 | Esser | |
| 5,613,971 A | 3/1997 | Lower et al. | |
| 5,620,449 A | 4/1997 | Faccioli et al. | |
| 5,643,273 A * | 7/1997 | Clark | A61B 17/1714 |
| | | | 606/102 |
| 5,766,174 A | 6/1998 | Perry | |
| 5,766,221 A | 6/1998 | Benderev et al. | |
| 5,772,662 A | 6/1998 | Chapman et al. | |
| 5,855,519 A | 1/1999 | Kadota | |
| 5,855,579 A | 1/1999 | James et al. | |
| 5,891,150 A | 4/1999 | Chan | |
| 5,919,193 A | 7/1999 | Slavitt | |
| 5,968,050 A | 10/1999 | Torrie | |
| 5,968,650 A | 10/1999 | Tennent et al. | |
| 5,993,456 A | 11/1999 | Speitling et al. | |
| 6,039,739 A | 3/2000 | Simon | |
| 6,048,343 A | 4/2000 | Mathis et al. | |
| 6,105,269 A * | 8/2000 | Kondrat | A61B 5/4504 |
| | | | 33/512 |
| 6,120,511 A | 9/2000 | Chan | |
| 6,200,685 B1 | 3/2001 | Davidson | |
| 6,270,499 B1 | 8/2001 | Leu et al. | |
| 6,287,313 B1 | 9/2001 | Sasso | |
| 6,325,583 B1 | 12/2001 | Mattle et al. | |
| 6,436,100 B1 | 8/2002 | Berger | |
| 6,520,969 B2 | 2/2003 | Lambrecht et al. | |
| 6,562,046 B2 | 5/2003 | Sasso | |
| 6,579,293 B1 | 6/2003 | Chandran | |
| 6,656,189 B1 * | 12/2003 | Wilson | A61B 17/1703 |
| | | | 606/97 |
| 6,673,076 B2 | 1/2004 | Deloge et al. | |
| 6,692,503 B2 | 2/2004 | Foley et al. | |
| 6,719,801 B1 | 4/2004 | Holt | |
| 6,746,453 B2 | 6/2004 | Deloge et al. | |
| 6,783,535 B2 | 8/2004 | Deloge et al. | |
| 6,887,243 B2 | 5/2005 | Culbert | |
| 6,908,465 B2 | 6/2005 | von Hoffmann et al. | |
| 6,981,974 B2 | 1/2006 | Berger | |
| 7,033,365 B2 | 4/2006 | Powell et al. | |
| 7,060,070 B1 | 6/2006 | Anastopoulos et al. | |
| 7,077,847 B2 | 7/2006 | Pusnik et al. | |
| 7,131,974 B2 | 11/2006 | Keyer et al. | |
| 7,147,643 B2 | 12/2006 | Robioneck et al. | |
| 7,175,632 B2 | 2/2007 | Singhatat et al. | |
| 7,179,632 B2 | 2/2007 | Williams et al. | |
| 7,229,448 B2 | 6/2007 | Goble et al. | |
| 7,232,443 B2 | 6/2007 | Zander et al. | |
| 7,311,710 B2 | 12/2007 | Zander | |
| 7,425,213 B2 | 9/2008 | Orbay | |
| 7,549,994 B2 | 6/2009 | Zander et al. | |
| 7,717,947 B1 | 5/2010 | Wilberg et al. | |
| 7,722,611 B2 | 5/2010 | Cavallazzi et al. | |
| 7,753,914 B2 | 7/2010 | Ruhling et al. | |
| 7,780,667 B2 | 8/2010 | Watanabe et al. | |
| 7,799,030 B2 | 9/2010 | Watanabe et al. | |
| 7,815,647 B2 | 10/2010 | Volzow | |
| 7,837,689 B2 | 11/2010 | Leyden et al. | |
| 7,901,410 B2 | 3/2011 | Bigdeli-Issazadeh et al. | |
| 7,918,853 B2 | 4/2011 | Watanabe et al. | |
| 7,927,340 B2 | 4/2011 | Hart | |
| 7,981,114 B2 | 7/2011 | Zander | |
| 7,985,222 B2 | 7/2011 | Gall et al. | |
| 8,034,056 B2 | 10/2011 | Fencl et al. | |
| 8,034,114 B2 | 10/2011 | Reiley | |
| 8,048,164 B2 | 11/2011 | Reiley | |
| 8,070,786 B2 | 12/2011 | Huebner et al. | |
| 8,092,505 B2 | 1/2012 | Sommers | |
| 8,118,810 B2 | 2/2012 | Prien | |
| 8,157,802 B2 | 4/2012 | Elghazaly et al. | |
| 8,187,281 B2 | 5/2012 | Cresina et al. | |
| 8,206,389 B2 | 6/2012 | Huebner et al. | |
| 8,211,107 B2 | 7/2012 | Parks et al. | |
| 8,211,108 B2 | 7/2012 | Matityahu | |
| 8,241,286 B2 | 8/2012 | Metzinger et al. | |
| 8,257,354 B2 | 9/2012 | Metzinger et al. | |
| 8,277,450 B2 | 10/2012 | Dees, Jr. et al. | |
| 8,303,589 B2 | 11/2012 | Tyber et al. | |
| 8,313,487 B2 | 11/2012 | Tyber et al. | |
| 8,313,492 B2 | 11/2012 | Wong et al. | |
| 8,328,806 B2 | 12/2012 | Tyber et al. | |
| 8,328,807 B2 | 12/2012 | Brigido | |
| 8,343,199 B2 | 1/2013 | Tyber et al. | |
| 8,382,808 B2 | 2/2013 | Wilberg et al. | |
| 8,414,584 B2 | 4/2013 | Brigido | |
| 8,449,543 B2 | 5/2013 | Pool et al. | |
| 8,491,593 B2 | 7/2013 | Prien et al. | |
| 8,540,114 B2 | 9/2013 | Sarson | |
| 8,540,714 B2 | 9/2013 | Gordon et al. | |
| 8,540,715 B2 | 9/2013 | Piraino | |
| 8,551,093 B2 | 10/2013 | Roth et al. | |
| 8,579,947 B2 | 11/2013 | Wu | |
| 8,591,517 B2 | 11/2013 | Metzinger et al. | |
| 8,623,060 B2 | 1/2014 | Vlahos et al. | |
| 8,663,224 B2 | 3/2014 | Overes et al. | |
| 8,668,225 B2 | 3/2014 | Yamaki et al. | |
| 8,668,725 B2 | 3/2014 | Smisson, III et al. | |
| 8,685,034 B2 | 4/2014 | Giersch et al. | |
| 8,715,284 B2 | 5/2014 | Culbert | |
| 8,715,293 B2 | 5/2014 | Vandewalle | |
| 8,764,752 B2 | 7/2014 | Buettler et al. | |
| 8,764,763 B2 | 7/2014 | Wong et al. | |
| 8,771,271 B2 | 7/2014 | Overes | |
| 8,771,282 B2 | 7/2014 | Blain et al. | |
| 8,771,283 B2 | 7/2014 | Larsen et al. | |
| 8,784,430 B2 | 7/2014 | Kay et al. | |
| 8,821,499 B2 | 9/2014 | Iannotti et al. | |
| 8,864,771 B2 | 10/2014 | Buscher et al. | |
| 9,033,987 B2 | 5/2015 | Hanson et al. | |
| 9,107,709 B2 | 8/2015 | Wieland et al. | |
| 9,259,257 B2 | 2/2016 | Bagga et al. | |
| 9,386,996 B2 | 7/2016 | Hanson et al. | |
| 9,408,648 B2 | 8/2016 | Culbert | |
| 9,427,242 B2 | 8/2016 | Kam | |
| 9,463,034 B2 | 10/2016 | Wong et al. | |
| 9,468,449 B2 | 10/2016 | Smith | |
| 9,498,370 B2 | 11/2016 | Taylor et al. | |
| 9,517,107 B2 | 12/2016 | Blau et al. | |
| 9,592,064 B2 | 3/2017 | Biedermann et al. | |
| 9,775,639 B2 | 10/2017 | Hanson et al. | |
| 9,814,473 B2 | 11/2017 | Cummings et al. | |
| 9,936,994 B2 | 4/2018 | Smith et al. | |
| 9,949,745 B2 | 4/2018 | Bouduban et al. | |
| 10,165,963 B2 | 1/2019 | Kaiser et al. | |
| 2006/0206044 A1 | 9/2006 | Simon | |
| 2008/0058829 A1 | 3/2008 | Buscher et al. | |
| 2014/0046384 A1 | 2/2014 | Horwitz | |
| 2014/0249536 A1 | 9/2014 | Jajeh | |
| 2016/0120554 A1 | 5/2016 | Wieland et al. | |
| 2016/0183995 A1 | 6/2016 | Zrinski et al. | |
| 2016/0310191 A1 | 10/2016 | Seykora et al. | |
| 2016/0367270 A1 | 12/2016 | Garlock et al. | |
| 2017/0172638 A1 | 6/2017 | Santrock et al. | |

OTHER PUBLICATIONS

Mendicino et al., "Technical considerations for surgical intervention of Jones fractures", The Journal of Foot and Ankle Surgery, vol. 52, Issue 3, May-Jun. 2013, pp. 409-414.

Nunley, James A., "Fractures of the base of the fifth metatarsal", The Orthopedic Clinics of North America, Foot and Ankle Trauma, vol. 32, No. 1, pp. 171-180, Jan. 2001.

Wukich et al., "Failed Intramedullary Screw Fixation of a Proximal Fifth Metatarsal Fracture (Jones Fracture) in a Division I Athlete: A case report", The Foot and Ankle Online Journal, vol. 2, No. 6, Jun. 2009.

(56) References Cited

OTHER PUBLICATIONS

"Speed Shift: Continuous Active Compression Implant", BioMedical Enterprises, 2014, 2 pages.

* cited by examiner

INSTRUMENTATION AND METHOD FOR REPAIR OF A BONE FRACTURE

FIELD OF THE INVENTION

The present invention relates generally to devices for treating bone fractures, and in particular relates to instrumentation for the proper sizing and placement of an implant in the repair of bone fractures.

BACKGROUND OF THE INVENTION

The outcome of an orthopedic procedure is highly dependent on the accuracy of the determination of implant size and placement within the bones or bone parts that are the subject of the procedure. A large number of post-operative and intra-operative complications can result from the use of an incorrectly sized or poorly placed implant, including complications from implant breakage or loss of fixation subsequent to the procedure.

In attempting to achieve accurate implant selection and positioning, guiding devices have been developed for the preparation of bone to receive implants as well as to receive implants in view of specific indications or conditions. Many of these devices have been developed or adapted for use with relatively large joints or bones. However, these devices often do not assist in the placement of implants, in particular medical bone screws, through multiple small bones or bone fragments of limited size, as often required in some surgeries of the foot or hand. Lisfranc joint arthrodesis, calcaneo-cuboid arthrodesis or scaphoid fracture fixation are a few examples of hand and foot procedures in which there is a lack of adequate instrumentation for the correct sizing and placement of implants, especially minimally invasive or non-invasive instrumentation.

Jones fractures, i.e., proximal fifth metatarsal fractures, are another example of indications where there is a lack of such instrumentation. The most common surgical treatment of these fractures involves a bone screw inserted through the medullary cavity of the fractured bone. An implanted screw should be positioned in the center of the intramedullary cavity to achieve optimal fixation and to avoid potential bone damage. An implanted screw also should have a width large enough to have endosteal purchase but small enough to avoid bone splitting or cracks. The screw further should have sufficient length to have satisfactory purchase and adequate fracture-bridging but should be short enough to avoid opening the fracture gap due to straightening the bone during screw insertion.

Some sizing instruments, such as length and depth gauges have been included in orthopedic instrument kits for use with the placement of medical bone screws. Such instruments aid in determining the appropriate screw length but often not the appropriate cross-section, width, or diameter best matching a patient's anatomy and indication. Screw taps have been used to determine both the length and diameter of a bone screw. However, taps are compulsorily implant-specific as they should have the same thread characteristics as the corresponding screw implant. Moreover, being invasive instruments, taps having an oversized diameter may cause a procedure to be halted or detrimentally impact the performance of an inserted implant and may even cause irreversible bone damage.

Therefore, there is a need for an instrument that aids in properly sizing and placing an implant through multiple small bones or bone fragments of limited size in a non-invasive manner.

SUMMARY OF THE INVENTION

In accordance with an aspect of the invention, a device for assisting in the positioning and sizing of an implant may include an elongate member and a block. The elongate member may include length indicia at axial locations along a length of the elongate member for measuring a first distance from a predetermined datum of the elongate member. The block may be attached to and movable along the elongate member. The block may include width indicia for measuring a second distance in a direction transverse to the first distance.

In some arrangements, the block may be movable to at least all axial locations along the length of the elongate member that include the length indicia.

In some arrangements, a surface of the block may have a plurality of sections. Each of the sections may have a different width than the other sections that defines the width indicia of the block.

In some arrangements, the device may further include a cannulated sleeve having a length. In such arrangements, the elongate member may be in the form of an arm. A rear portion opposite a front portion of the elongate member may be attached to and may extend from the sleeve. The front portion of the elongate member may extend in a direction substantially parallel to the length of the sleeve.

In some arrangements, the sleeve may have at least a first diameter less than a second diameter of the sleeve. In such arrangements, the elongate member may include an aperture for receiving the first diameter of the sleeve.

In some arrangements, the elongate member may be rotatable about the sleeve such that either or both of the length and the width indicia are viewable in a plurality of angular positions of the arm.

In some arrangements, the device may include a retainer for holding the sleeve to the elongate member.

In some arrangements, the device may include a handle that may be attached to and may extend from the sleeve.

In some arrangements, the elongate member may define a slot.

In some arrangements, the block may have grooves on opposing sides of the block for receiving a thickness of the elongate member such that the block may slide within the slot. In this manner, when the block slides within the slot, the block may be maintained within the slot.

In some arrangements, either or both of the elongate member and the block may be at least partially radiopaque or radiolucent during radiographic viewing.

In some arrangements, at least one of the length indicia may be alignable with a position for insertion of a portion of the implant. In such arrangements, the block may be moveable to an axial location of the elongate member that is aligned with the position to which the portion of an implant is to be inserted.

In some arrangements, the elongate member may be rotatable about the sleeve. In such arrangements, the sleeve may include a plurality of indentations around a circumference of the sleeve. In such arrangements, the elongate member may include a body and may include an insertion element moveable relative to the body. In such arrangements, when the insertion element is in alignment with one of the indentations, a greater force may be required to rotate the elongate member about the sleeve than when the insertion element does not extend into any of the indentations.

In some arrangements, the insertion element of the elongate member and the indentations of the sleeve may form a detent assembly.

In some arrangements, the detent assembly may include a resilient element and a ball. In such arrangements, the resilient element may be located in a bore of the body of the elongate member and may be compressible between a base surface of the bore and the ball. In such arrangements, when the insertion element is in alignment with one of the indentations, the ball may extend into the aligned indentation.

In some arrangements, the insertion element may be a lever that may be pivotable about the body. When the lever is in a first position relative to the body, the lever may extend into the aligned indentation, and when the lever is in a second position relative to the body, the insertion element may not extend into the aligned indentation.

In some arrangements, the device may include a resilient member that may extend between a first surface of the body of the elongate member and a second surface of the lever of the elongate member. In such arrangements, the resilient member may bias the lever in the first position of the lever.

In some arrangements, the insertion element and the body may be spaced apart cantilevers extending from a main body of the elongate member. In such arrangements, the insertion element and the body may be defined by a central groove along a portion of the elongate member. In such arrangements, when the insertion element is in a first position relative to the body, the insertion element may extend into the aligned indentation, and when the lever is in the second position relative to the body, the insertion element may not extend into the aligned indentation.

In some arrangements, the device may include a resilient element between a first surface of the elongate member and a surface of the retainer. In such arrangements, the retainer may be fixedly attached to the sleeve. In such arrangements, the elongate member may be rotatable about the sleeve. In such arrangements, the sleeve may include a plurality of sleeve indentations, or the sleeve may include a plurality of sleeve bosses around a circumference of the sleeve. In such arrangements including the plurality of sleeve indentations, the elongate member may include an elongate member boss for receipt in each of the plurality of sleeve indentations. In such arrangements including the plurality of sleeve bosses, the elongate member may include an elongate member indentation for receipt of each of the sleeve bosses.

In such arrangements including the plurality of sleeve indentations, when the elongate member boss is received in one of the plurality of sleeve indentations, the resilient element may provide an axial force against the elongate member to hold a second surface of the elongate member opposite the first surface against a surface of the sleeve such that a greater rotational force is required to rotate the elongate member about the sleeve than when the elongate member includes the elongate member boss and the elongate member boss is not received in one of the plurality of sleeve indentations. In such arrangements including the plurality of sleeve indentations, the elongate member indentation is in receipt of one of the sleeve bosses, the resilient element may provide an axial force against the elongate member to hold a second surface of the elongate member opposite the first surface against a surface of the sleeve such that a greater rotational force is required to rotate the elongate member about the sleeve than when the elongate member includes the elongate member indentation and the elongate member indentation is not in receipt of one of the sleeve bosses.

In some arrangements, the first surface of the elongate member may be within a groove of the elongate member and the surface of the retainer may be within a groove of the retainer.

In some arrangements, a trigger may extend from the elongate member. In such arrangements, when the trigger is pulled from a first position to a second position, the elongate member may compress the resilient element such that the second surface of the elongate member may be held away from the surface of the sleeve to allow for rotation of the elongate member about the sleeve.

In some arrangements, the sleeve may include a groove around a circumference of the sleeve, and the elongate member may include a body and an insertion element moveable relative to the body for contact with a base surface of the groove. In such arrangements, when the insertion element is in contact with the base surface of the groove, a greater force may be required to rotate the elongate member about the sleeve than when the insertion element is not in contact with the base surface of the groove.

In some arrangements, the insertion element may be an elongated screw device.

In accordance with an aspect of the invention, a system for assisting in the positioning and sizing of an implant may include an elongate member, a block, a cannulated sleeve, and a guide wire. The elongate member may be in the form of an arm and may include length indicia at axial locations along a length of the elongate member for measuring a first distance from a predetermined datum of the elongate member. The block may be attached to and may be movable along the elongate member. The block may include width indicia for measuring a second distance in a direction transverse to the first distance. The cannulated sleeve may have a length. A rear portion opposite a front portion of the elongate member may be attached to and may extend from the sleeve in which the front portion of the elongate member may extend in a direction substantially parallel to the length of the sleeve. The elongate member may include, i.e., define, a slot. The guide wire may extend through the sleeve, and an end of the guide wire may be visible through the slot of the elongate member.

In some arrangements, the elongate member may be radiographically viewable, and an end of the guide wire may be radiographically viewable through the slot of the elongate member.

In accordance with an aspect of the invention, a process for assisting in the positioning relative to at least one bone and sizing of an implant is provided. In such a process, a block may be moved along an elongate member to an axial location along the elongate member at which a first width indicium of a set of width indicia may be aligned with a position to which a portion of the implant is to be inserted. The width indicium may correspond to an appropriate width of the portion of the implant. The elongate member may include a set of length indicia at axial locations along a length of the elongate member for measuring a distance from a predetermined datum of the elongate member. A first length indicium of the length indicia may be aligned with the width indicium corresponding to an appropriate depth for insertion of the portion of the implant. In such a process, the elongate member may be positioned over the one or more bones being positioned and sized.

In some arrangements, the implant may be inserted into the one or more bones being positioned and sized to the axial location of the first width indicium after moving the block.

In some arrangements, the implant may be a screw.

In some arrangements, a guide wire may be inserted into the one or more bones being positioned and sized, and the implant may be received over the guide wire.

In some arrangements, the elongate member may be in the form of an arm. In such arrangements, rear portion opposite a front portion of the elongate member may be attached to and may extend from a sleeve. In such arrangements, the front portion of the elongate member may extend in a direction substantially parallel to the length of the sleeve. In such arrangements, a guide wire may be received through an aperture of the sleeve.

In some arrangements, the sleeve may have at least a first diameter less than a second diameter of the sleeve. In such arrangements, the elongate member may include an aperture. In such arrangements, the first diameter of the sleeve may be received through the aperture of the elongate member.

In some arrangements, a retainer may be received on the sleeve such that the elongate member may be held in position on the sleeve.

In some arrangements, the elongate member may be rotated about the sleeve from a first position in which at least some of the sets of length and width indicia are viewable to a second position in which such sets of length and width indicia are viewable.

In some arrangements, the elongate member may define a slot. In such arrangements, the block may be slideable within the slot to the axial location of the elongate member aligned with the position to which the portion of the implant is to be inserted.

In some arrangements, a guide wire may be inserted into the one or more bones being positioned and sized. In such arrangements, an end of the guide wire may be visible through the slot of the elongate member in order to aid in determining the orientation of the guide wire.

In accordance with an aspect of the invention, a process for assisting in the positioning relative to at least one bone and sizing of an implant is provided. In such a process, an elongate member may be positioned over the one or more bones being positioned and sized. A first length indicium of a set of length indicia at axial locations along the elongate member may be matched to a depth for insertion of a portion of the implant. The set of length indicia may correspond to respective distances from a predetermined datum of the elongate member. A block may be moved along the elongate member such that a first width indicium of a set of width indicia of the elongate member may be aligned with the first length indicium. An implant having a width corresponding to the first width indicium and a length corresponding to the first length indicium may be selected. The implant may be inserted into the one or more bones being positioned and sized such that the portion of the implant is located substantially near the first length indicium.

In accordance with an aspect of the invention, an elongate member for assisting in the positioning and sizing of an implant may include a radiolucent body either or both of radiopaque length indicia and radiopaque width indicia. The length indicia may be located at axial locations along a length of the radiolucent body to provide designations for measuring a first distance from a predetermined datum of the body. The width indicia may provide designations for measuring a second distance in a direction transverse to the first distance. The width indicia may be parallel lines extending along a top surface of the elongate member in a direction parallel to the longitudinal axis of the elongate member. The width indicia may be radiographically viewable by a user of the elongate member.

DETAILED DESCRIPTION

As used herein, the terms "proximal" and "distal," and variations thereof, refer to the perspective of a physician, other medical provider, or other user of the devices and instrumentation described herein. The terms "superior" and "inferior," and variations thereof, as used herein refer to locations closer to the crown of a patient's head and the base of a patient's feet, respectively. The terms "medial" and "lateral," and variations thereof, as used herein refer to locations closer to a patient's heart and a patient's arms, respectively.

Figure 1A:
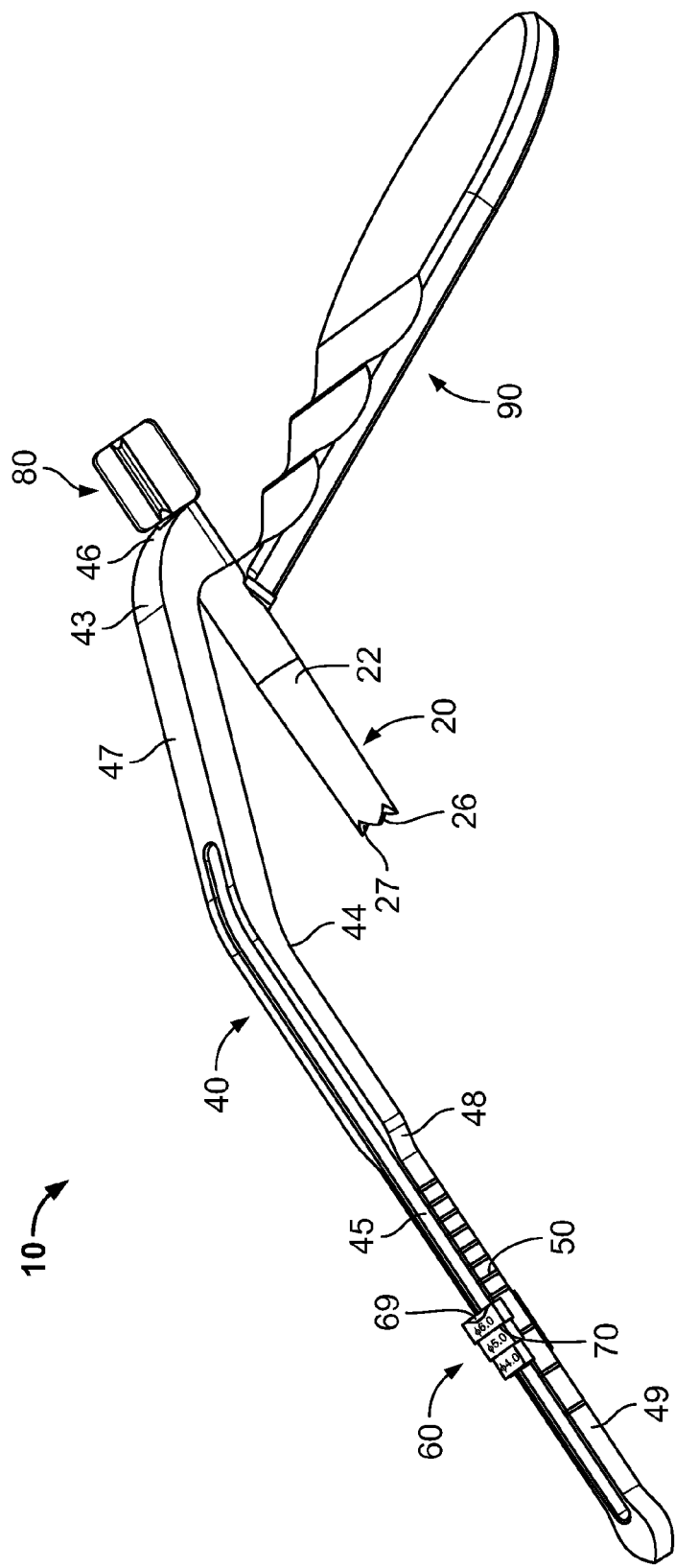
FIG. 1A is a perspective view of an aiming device in accordance with an embodiment.
Figure 1B:
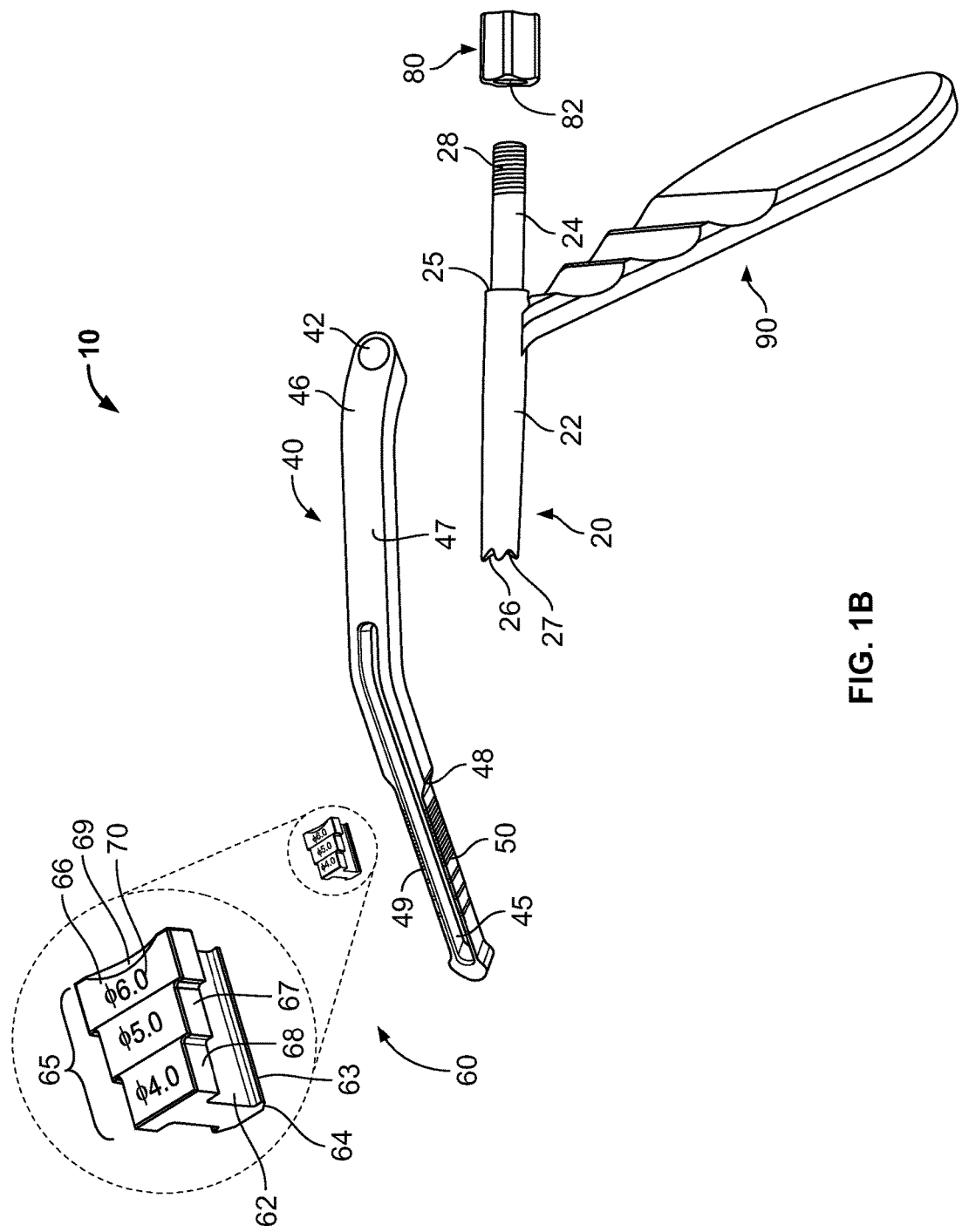
FIG. 1B is an exploded view of the aiming device of FIG. 1A.

Referring now to the drawings, as shown in FIGS. 1A and 1B, aiming device 10 is an assembly for alignment and sizing of implants, such as screws. Aiming device 10 includes sleeve 20, arm 40, block 60, retainer 80, and handle 90. Sleeve 20 is an elongated tube that includes a distal section 22 having a larger outside diameter than a proximal section 24 to define a step 25. A distal-most end of sleeve 20 includes serrations or distally extending teeth 26 for providing anti-slip engagement with bone.

A proximal-most end of proximal section 24 of sleeve 20 includes threads 28 for threaded engagement with retainer 80, which may be a threaded nut, having threaded inner diameter 82. Sleeve 20 includes aperture 27 which may be in the form of a hole extending through the length of sleeve 20. In this manner, aiming device 10 may be inserted over a first rod or shaft, such as but not limited to any of a guide wire, a Kirschner wire, a drill, a tap, and a countersink as described further herein, that may extend through aperture 27.

Handle 90 extends from sleeve 20 in a direction transverse to a longitudinal axis of sleeve 20 and may be used to manipulate the position or orientation of sleeve 20. Handle 90 may be welded to sleeve 20. Either or both of sleeve 20 and handle 90 may be, but are not limited to being, made of any of metal, radiopaque material, plastic, and radiolucent material, so long as the sleeve and handle have sufficient stiffness to avoid flexure during use.

Still referring to FIGS. 1A and 1B, arm 40 is an elongate member substantially in the form of a bent rod. Arm includes aperture 42 on its proximal end into which proximal section 24 of sleeve 20 may be inserted. A longitudinal axis of aperture 42 of arm 40 is the same or approximately the same as the longitudinal axis of aperture 27 of sleeve 20. Arm 40 includes curved or bent portions 43, 44 at selected positions along its length that define proximal section 46, central section 47, and distal section 48. In this manner, arm 40 extends away from sleeve 20 a predetermined distance in a direction transverse to the longitudinal axis of sleeve 20. Such a distance may be determined based on a distance necessary to clear other objects, such as a patient's skin, surrounding sleeve 20. This clearance distance may be but is not limited to being a distance in a range between and including 1 cm and 20 cm, and preferably in a range between and including 1 cm and 5 cm. Providing this clearance may be of particular interest in situations in which accurate placement of an implant is desired in multiple planes.

Arm 40 includes a slot 45 which extends from central section 47 at a position near its longitudinal center to a position near a distal end of distal section 48. As shown, thin wall section 49 of distal section 48 defines a portion of slot 45 that may have a reduced wall thickness relative to a wall thickness of other portions of arm 40 that define slot 45. Thin wall section 49 includes length indicia 50 marked on an outer surface along a length of sleeve 20 that may be used to indicate insertion depth or other distance parameters to be measured.

As illustrated by FIG. 1A, block 60 may be inserted within slot 45 of arm 40 during assembly of aiming device 10. As best shown in FIG. 1B, block 60 is generally in the form of an I-beam having an elongated central section 62 bounded by lower base 63 opposite upper base 65. In this manner, central section 62 may slide within and along at least a majority of the length of slot 45. Put another way, central section 62, lower base 63, and upper base 65 define opposing grooves of block 60 in which such grooves may receive thin wall section 49 of arm 40 when block 60 is inserted within slot 45. Lower base 63 includes opposing chamfers 64. In this manner, lower base 63 slightly elastically deforms during insertion of block 60 into slot 45 of arm 40.

Block 60 may be but is not limited to being held in the arm by a press-fit. In the example shown, the width of central section 62 of block 60 is larger than the width of slot 45 of sleeve 20. In this manner, the slider may be held in place when external forces, such as those applied by a user of aiming device 10, are applied.

As in the example shown, upper base 65 of block 60 is delineated into three width measurement sections (66, 67, 68). Each of the three sections (66, 67, 68) has a different width as measured in a transverse direction to the longitudinal axis of the sleeve 20. The measured width of each of the three sections is marked onto each of the three sections to provide width indicia 70.

When block 60 is inserted into sleeve 20, widest section 66 is the most proximal section and narrowest section is the most distal section. Widest section 66 includes indentation 69 that may provide an ergonomic surface for pressing against block 60 so as to cause block 60 to slide within sleeve 20.

As best shown in FIG. 1A, when proximal section 24 of sleeve 20 is inserted within aperture 42 of arm 40, mating threads (not shown) of retainer 80 may be threaded onto threads 28 of sleeve 20 to compress proximal section 46 of arm 40 against step 25 of sleeve 20. In this manner, arm 40 may be held in a predetermined axial position relative to sleeve 20. When retainer 80 is tightened sufficiently, arm 40 may be fixed rotationally such that it does not rotate relative to sleeve 20.

Figure 2A:
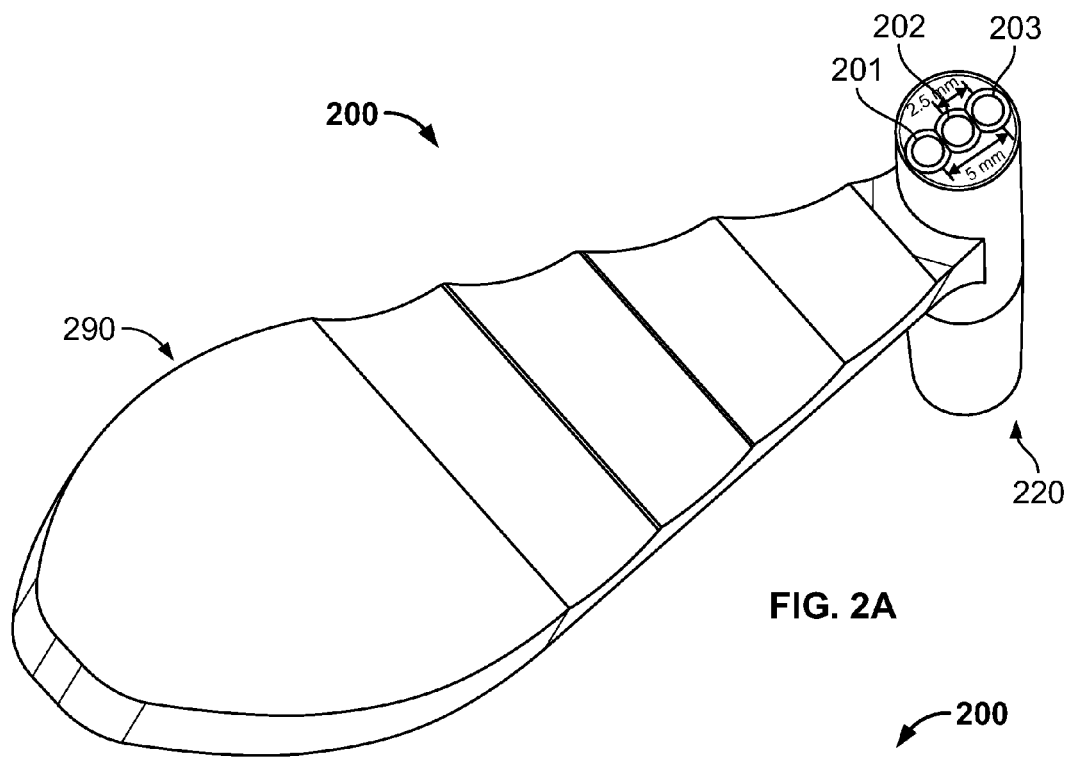
FIG. 2A is a perspective view of an offset device in accordance with an embodiment.
Figure 2B:
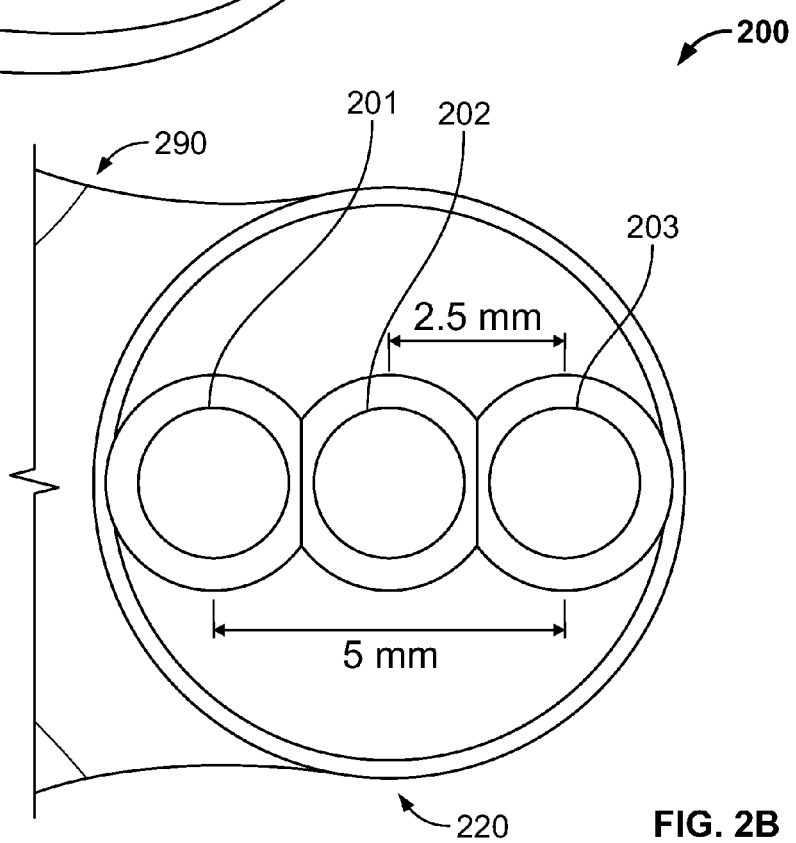
FIG. 2B is a plan view of a sleeve and portion of a handle of the offset device of FIG. 3A.

Referring now to FIGS. 2A and 2B, offset device 200, which may be used during a surgical procedure along with aiming device 10, as described further herein, includes a sleeve 220 and handle 290 extending from sleeve 220 to provide an easy way to grip and maneuver aiming device 200. Sleeve 220 includes at least three parallel apertures (201, 202, 203), which in the example shown are in the form of holes extending through the length of sleeve 220. A central axis of each of outer apertures 201, 203 is disposed a predetermined distance from middle aperture 202 and thus a predetermined distance from each other. In the example shown, the central axis of outer aperture 203 is set at or approximately at 2.5 mm from the central axis of middle aperture 202 and is set at or approximately at 5 mm from the central axis of outer aperture 201. In this manner, offset device 200 may be inserted over a first rod or shaft, such as but not limited to any of a guide wire, a drill, a tap, and a countersink as described further herein, that may extend through one of apertures (201, 202, 203) and then a second rod or shaft may be inserted into another of apertures (201, 202, 203) such that the second rod or shaft may be spaced from the first rod or shaft by the distance between the apertures through which the first and second rods extend.

Figure 3:
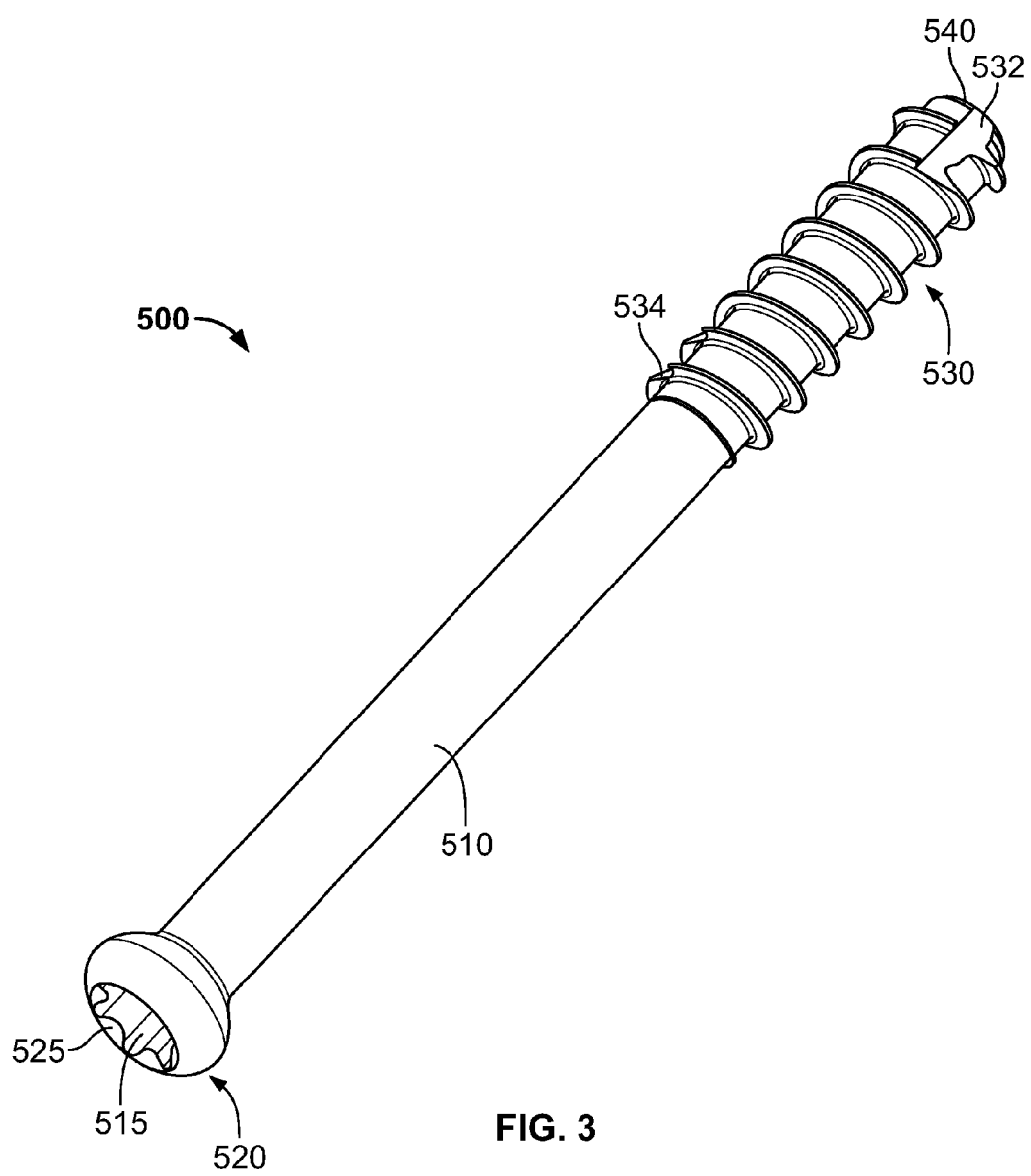
FIG. 3 is a perspective view of an implant in accordance with an embodiment.

As shown in FIG. 3, an implant 500, which in this example is in the form of a screw, includes unthreaded shank 510, head 520 extending from shank 510 on a proximal end of the shank, and threaded portion 530 extending from shank 510 on a distal end of the shank. Implant 500 is cannulated, as shown, to allow for a guide wire or other device to be received through an aperture 515 along a length of the implant. Shank 510 has a greater length than threaded portion 530. Implant 500 has a truncated, as opposed to a conical, tip 540 at its most distal end having the same or approximately the same outer diameter as shank 510.

Head 520 is bulbous in form with smooth sides extending from its proximal end to its distal end at its interface with shank 510. Head 520 has a relatively very low profile such that the head need only be implanted a short distance into a bone to be fully inserted into the bone. Head 520 includes an inner aperture 525 that has a profile for receipt of a TORX® driving connection, although other profiles, such as but not limited to those for hex driver connections may be used instead.

Threaded portion 530 of implant 500 may one or more, including as in this example three, self-tapping grooves 532 around a portion of a circumference of the implant at the distal end of the implant which may reduce the required insertion torque of the implant. Threaded portion 530 includes reverse cutting flutes 534 at a proximal end of the threaded portion that reduce the torque otherwise needed to removal an implant after bone healing should such removal be needed.

Figure 4:
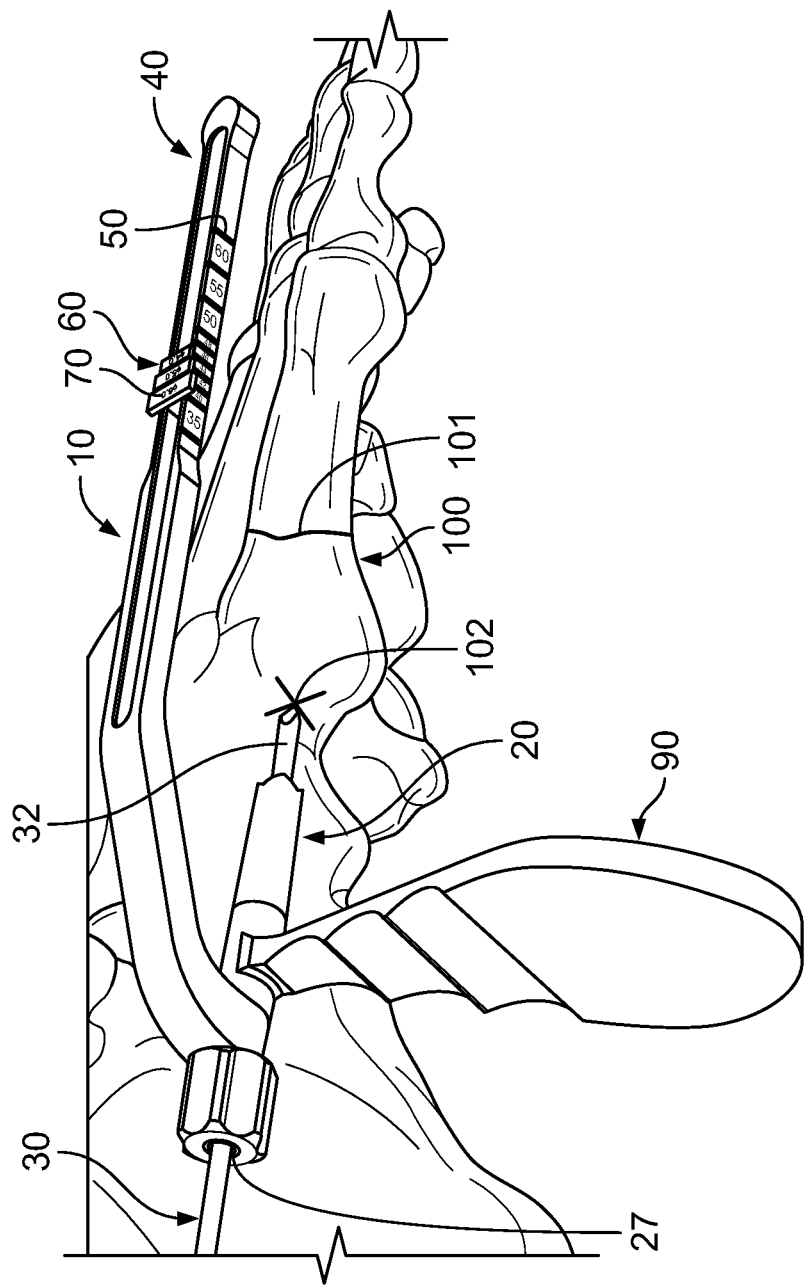
FIGS. 4-8 are perspective views illustrating a surgical procedure in accordance with an embodiment.

With reference to FIG. 4, aiming device 10 may be used during surgical procedures to repair bone fractures such as, but not limited to, fractures of the fifth metatarsal of a human foot. During a procedure to repair Jones fracture 101, a 1-2 cm incision is made to a patient's skin proximal to the cuboid, i.e., the base or tuberosity, of fifth metatarsal bone 100. Guide wire 30, which may have but is not limited to having, an outer diameter of 2.0 mm, is inserted through the incision such that its tip 32, which is pointed, is positioned at an entry point 102 (identified by an "X" in FIG. 4) at a superior and medial location on the base of bone 100. At this point, aiming device 10 is placed over guide wire 30 such that the guide wire extends through aperture 27 of sleeve 20. Handle 90 of aiming device 10 may be used to adjust the position of and orient tip 32 of guide wire 30 relative to a longitudinal axis of bone 100.

Figure 5:
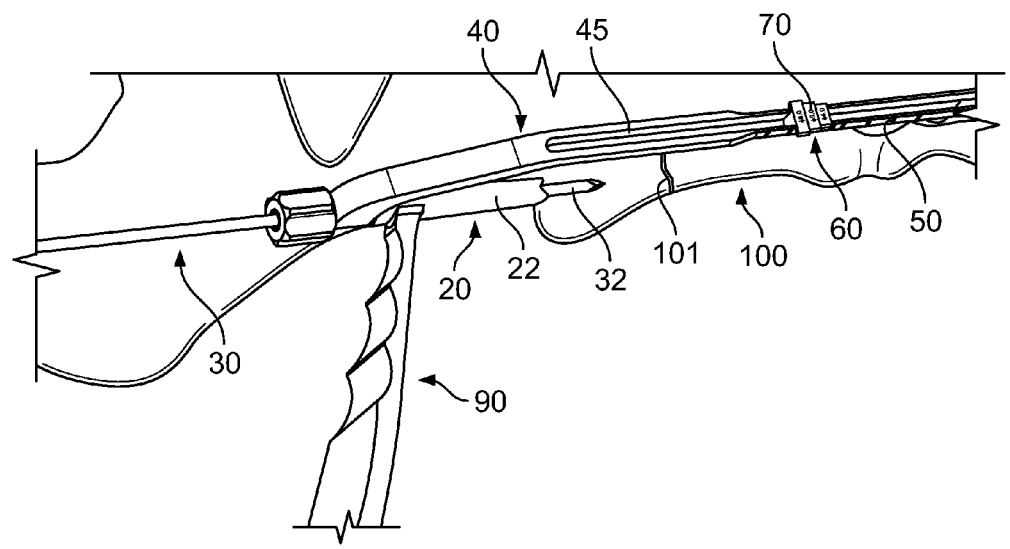

As illustrated in FIG. 5, guide wire 30 may then be inserted, such as by a powered rotary tool known to those of skill in the art, into bone 100 approximately 1-2 mm so as to cross the epiphyseal cortex. At this point, aiming device 10 is placed over guide wire 30 such that the guide wire is received through cannulated sleeve 20. In this regard, a torque applied on handle 90 will tend to modify an insertion angle of sleeve 20 by deforming the bone material surrounding the distal end of sleeve 20.

Figure 6:
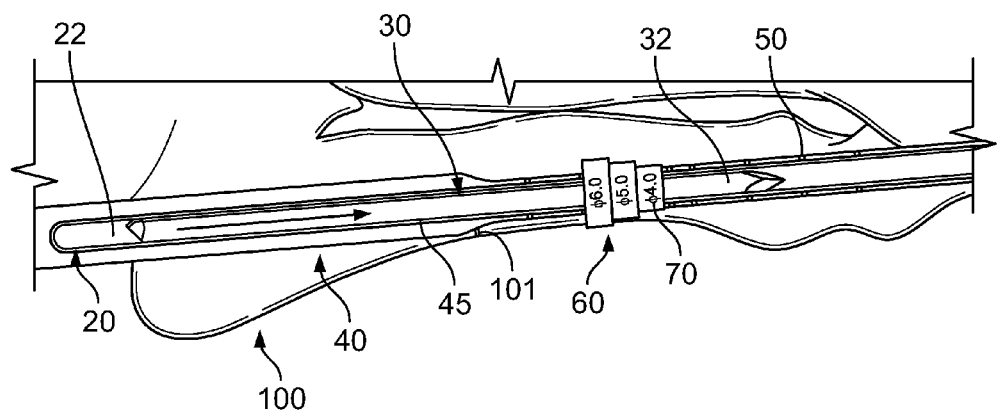

As best shown in FIG. 6, during the Jones fracture repair procedure, arm 40 may be rotated about sleeve 20 so as to be over the fifth metatarsal in a dorso-plantar position for viewing of bone 100 in a medial direction. In this manner, during fluoroscopy, distal section 22 of sleeve 20 and tip 32 of guide wire 30 may appear in the center of slot 45 of arm 40 in an anterior-posterior view. As in this example, the width of slot 45 may be greater than the width of guide wire 30 as well, as other devices to be viewed through the slot, to determine either or both of position and orientation of such devices.

Referring to FIGS. 5 and 6, arm 40 may be made of a radiopaque metallic material, such as stainless steel, to be visible with X-rays fluoroscopic imaging equipment generally available in operating rooms. With arm 40 rotated to an angular orientation relative to sleeve 20 such that block 60 is viewable during fluoroscopy, block 60 may be moved to an axial location along slot 45 of arm 40 corresponding to an axial location along bone 100 at which tip 540 of screw 500 (not shown in FIGS. 5 and 6) should lie upon insertion of screw 500, as described further herein. Preferably, this axial location should align with the middle of the diaphysis. Once block 60 is set at the preferred axial location, an appropriate major diameter of screw 500 may be determined. As best shown in FIG. 6, the appropriate major diameter of screw 500 in this example would likely be 5 mm. A major diameter of 6 mm would leave insufficient thickness of bone between screw 500 and the outermost layer of bone material of the fifth metatarsal. A major diameter of 4 mm, in contrast, may be workable but may not maximize the bending strength or anchorage of the assembly of screw 500 with bone 100 in comparison to the 5 mm screw.

Figure 7:
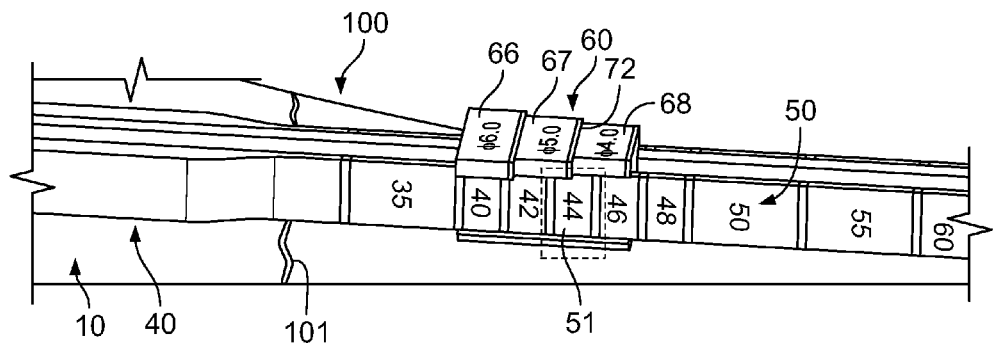

As illustrated in FIG. 7, once block 60 is set at the appropriate axial location, an appropriate screw length is determined by alignment of indicia 51 of length indicia 50 with a distal edge 72 of middle section 67 of width measurement section (66, 67, 68). This alignment is demonstrated by the dashed rectangle shown in FIG. 7.

With reference again to FIGS. 5 and 6, arm 40 may be rotated laterally to a superior position (not shown) relative to bone 100 for viewing of bone 100 in an inferior direction. In this manner, the angle of insertion of guide wire 30 may be checked by fluoroscopy showing a lateral view and wire 30 may be adjusted, if necessary. The appropriate screw length and major diameter of screw 500 may also be reassessed, as described previously herein, if necessary. At this juncture, guide wire 30 is advanced into the intramedullary canal of bone 100, as shown. Aiming device 10 then may be slid proximally along guide wire 30 and removed from assembly with the guide wire.

Figure 8:
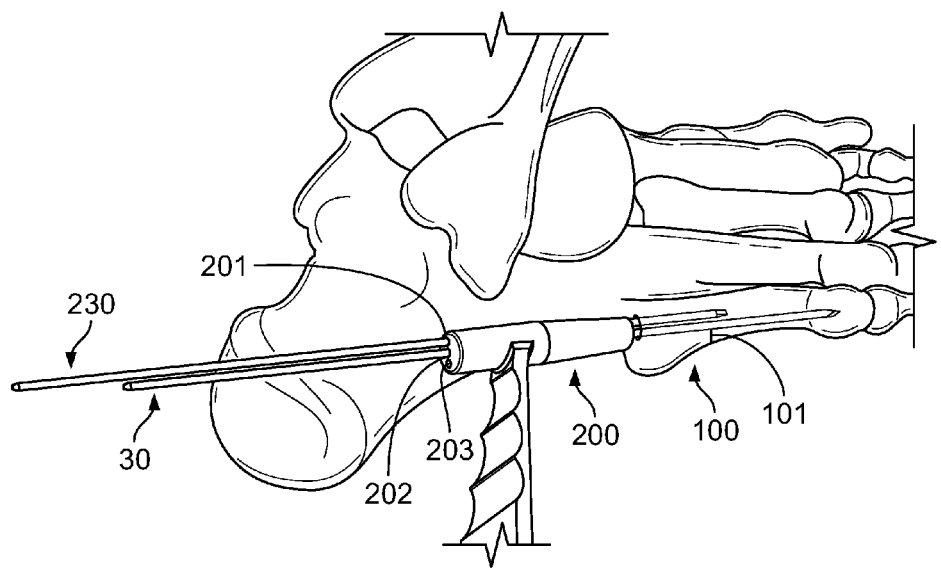

As shown in FIG. 8, when guide wire 30 has been inserted at an appropriate angle relative to the intramedullary canal of bone 100 but is not appropriately centered within the canal, offset device 200 is placed over guide wire 30 such that guide wire 30 passes through middle aperture 202 of parallel apertures (201, 202, 203). While guide wire 30 is received in offset device 200, second guide wire 230 may be inserted, such as by a rotary power tool, into another one of parallel apertures (201, 202, 203), in this example outer aperture 201. In this manner, second guide wire 230 is offset from guide wire 30 the distance the longitudinal axis of middle aperture 202 is offset from outer aperture 201.

Figure 9:
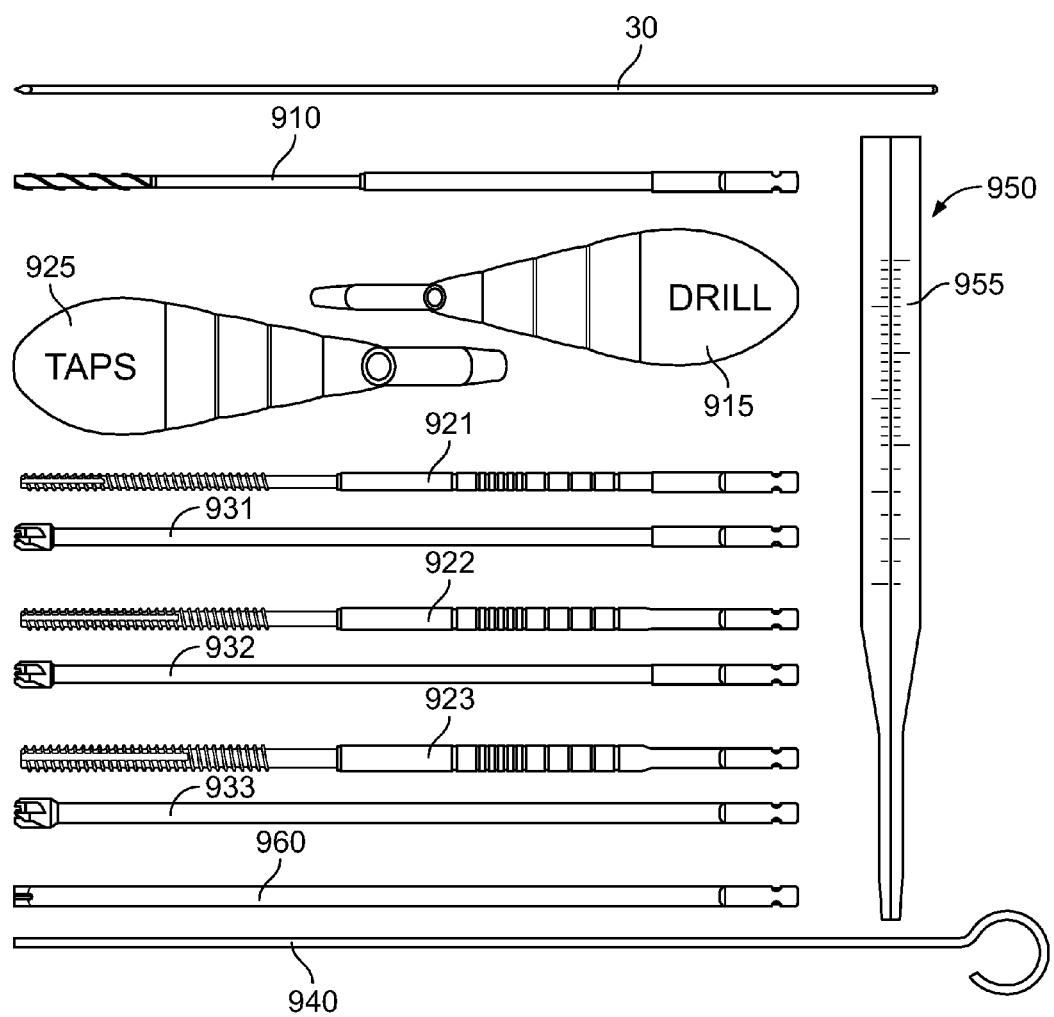
FIG. 9 is a perspective view of various instruments for use in preparing a bone for insertion of an implant.

Referring now to FIG. 9, various instruments may be used in preparing a bone for insertion of either or both of guide wire 30 and an implant such as but not limited to screw 500. Drill 910 may be used to drill a bore in the intramedullary canal of the fifth metatarsal. Drill 910 may be inserted into cannulated drill protecting sleeve 915 for maintaining alignment of the drill during the drilling operation. A series of taps (921, 922, 923) of increasing major diameter may be used to tap the bore drilled by drill 910. Each of the series of taps (921, 922, 923) may be inserted into corresponding cannulated tap protecting sleeve 925 for maintaining alignment of the tap during the tapping operation. Tap protecting sleeve 925 may have an inner diameter sufficient to receive the major diameter of the corresponding tap (921, 922, 923). Each tap (921, 922, 923) may have a major diameter corresponding to the major diameter of the appropriate screw 500 chosen for a fracture repair procedure. In this regard, a series of countersinks (931, 932, 933) of increasing major diameter may be used to form a pilot counterbore at the entrance of the bore drilled by drill 910. In this manner, a distal surface of head 520 of screw 500 may be set slightly below the base of bone 100.

Cleaning stylet 940 may be used to clean the drilled bore of removed bone material. Direct screw length gauge 950, which may include depth markings 955 along its length, may be inserted over guide wire 30 and advanced into a drilled bore until it reflects the desired screw insertion depth. When length gauge 950 is in this position, the final screw position may correspond with a distal tip position of guide wire 30 aligned with depth markings 55. Screwdriver 960 may be used to thread the appropriate screw 500 into the drilled and tapped bore. Any or all of the instruments shown in FIG. 9 as well as aiming device 10 may be included in a kit, which may be a sealed kit.

Figure 10:
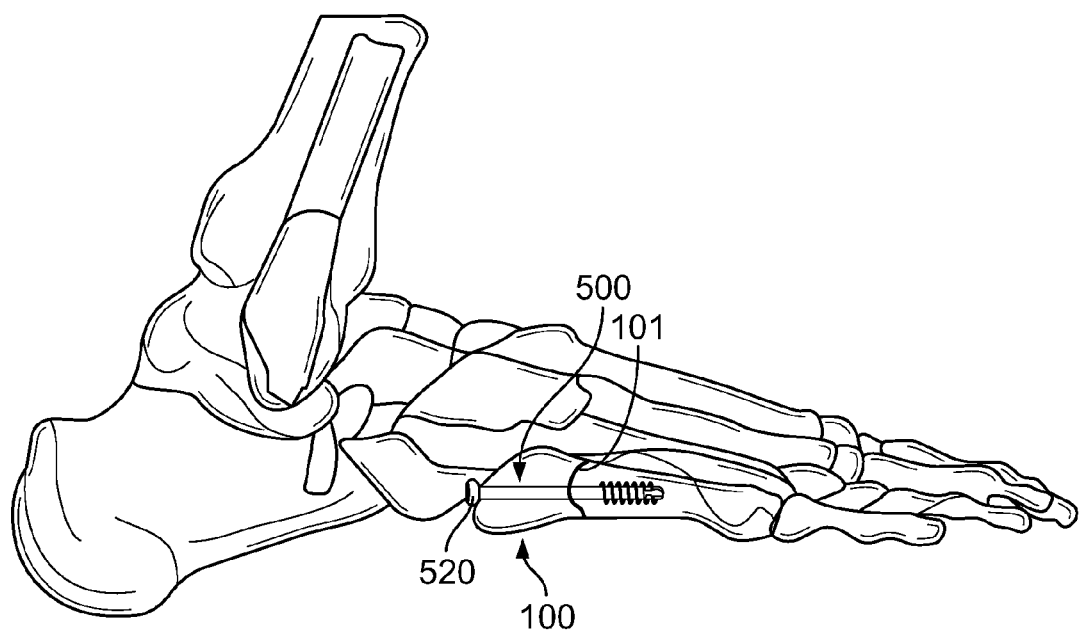
FIG. 10 is a perspective view of the implant of FIG. 3 shown at full insertion into a bone during a bone fracture repair procedure.
Figure 11A:
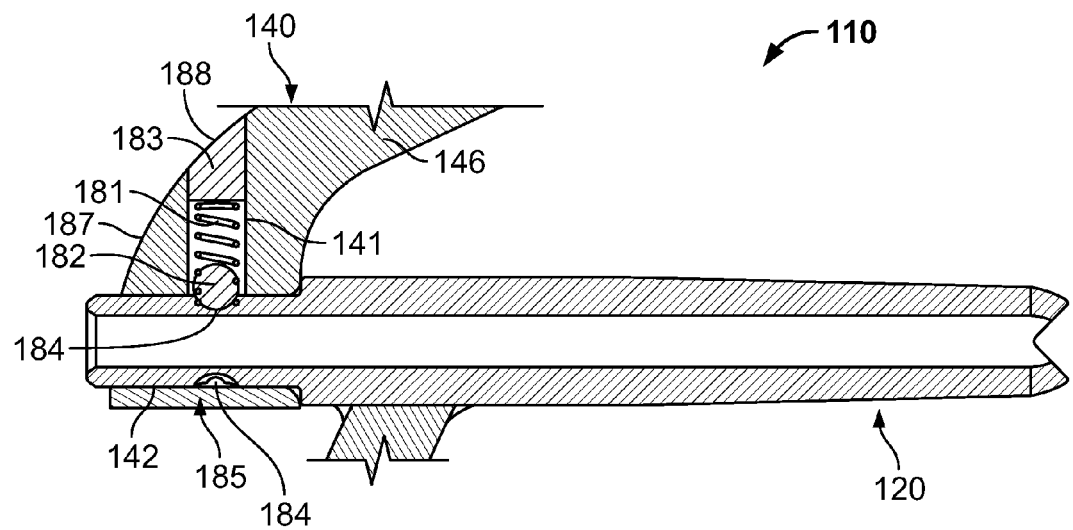
FIG. 11A is a cross-sectional view of a portion of an aiming device in accordance with another embodiment.
Figure 11B:
FIG. 11B is an elevation view of a portion of a sleeve of the aiming device of FIG. 11A.

As shown in FIG. 10, cannulated screw 500 may be inserted into drilled and tapped bore of the fifth metatarsal such that the distal surface of head 520 of screw 500 sits flush against the counterbore prepared using the countersinks (931, 932, 933). In this manner, screw 500 performs osteosynthesis of bone 100 across fracture 101.

Referring now to FIGS. 11A-16B, in some alternative arrangements, aiming device 110, 210, 310, 410, 510, 610 may be substantially similar to aiming device 10 with the exception of features relating to the attachment of the arm to the sleeve. In the arrangement shown in FIGS. 11A and 11B, aiming device 110 includes sleeve 120 and arm 140. Arm 140 includes bore 141 extending through its proximal section 146 in a direction transverse to a longitudinal axis of sleeve 120 when arm 140 is assembled with the sleeve. Arm 140 includes resilient element 181, which as shown may be but is not limited to being a coiled spring, compressed between ball 182 and insert 183. Along with any of a series of indentations 184 in groove 185 extending around a circumference of sleeve 120 as shown in FIG. 11B, resilient element 181 and ball 182 form a detent assembly.

In this example, bore 141 extends through exterior surface 187 of proximal section 146 opposite aperture 142 of arm 140 into which sleeve 120 may be inserted. Insert 183 is press-fit, although in other arrangements may be attached by a fastener such as a screw, into bore 141 such that the insert generally remains in fixed position but is removable from bore 141. In this manner, resilient element 181 and ball 182 may be inserted into bore 141, and ball 182 may be further inserted into groove 185 of sleeve 120 when the sleeve is received in aperture 142. Insert 183 may be inserted into bore 141 such that upper surface 188 of insert 183 opposite an end of the insert contacting resilient element 181 is flush with exterior surface 187 of proximal section 146.

In an alternative arrangement (not shown), bore 141 may be substituted with a bore that extends only partially through the arm such that the bore does not pass through the exterior surface of the arm. In this manner, resilient element 181 may be compressed between an end surface of the alternative bore and ball 182.

When arm 140 is rotated about sleeve 120, arm 140 is more difficult to rotate when ball 182 is inserted into any one of indentations 184 than when ball 182 is in groove 185 but not in one of indentations 184. Indentations 184 may be set at any location about the circumference of groove 185, although preferably the indentations may be set at equally spaced-apart intervals corresponding to at least every 90 degrees about the groove, and the indentations could be set at least every 1 degree about the circumference of the groove. Intervals set at every 90 degrees provide an easy interchange between adjacent perpendicular visualization views, e.g., from an anterior-posterior view to a lateral view. In contrast, intervals set at every 1 degree provide for additional orientations of the arm relative to the sleeve and thus additional possible viewing angles. In light of the use of groove 185, aiming device 110 does not include a retainer, such as retainer 80, to retain arm 140 on sleeve 120. As such, sleeve 120 may be shorter than sleeve 20 of aiming device 10.

Figure 12:
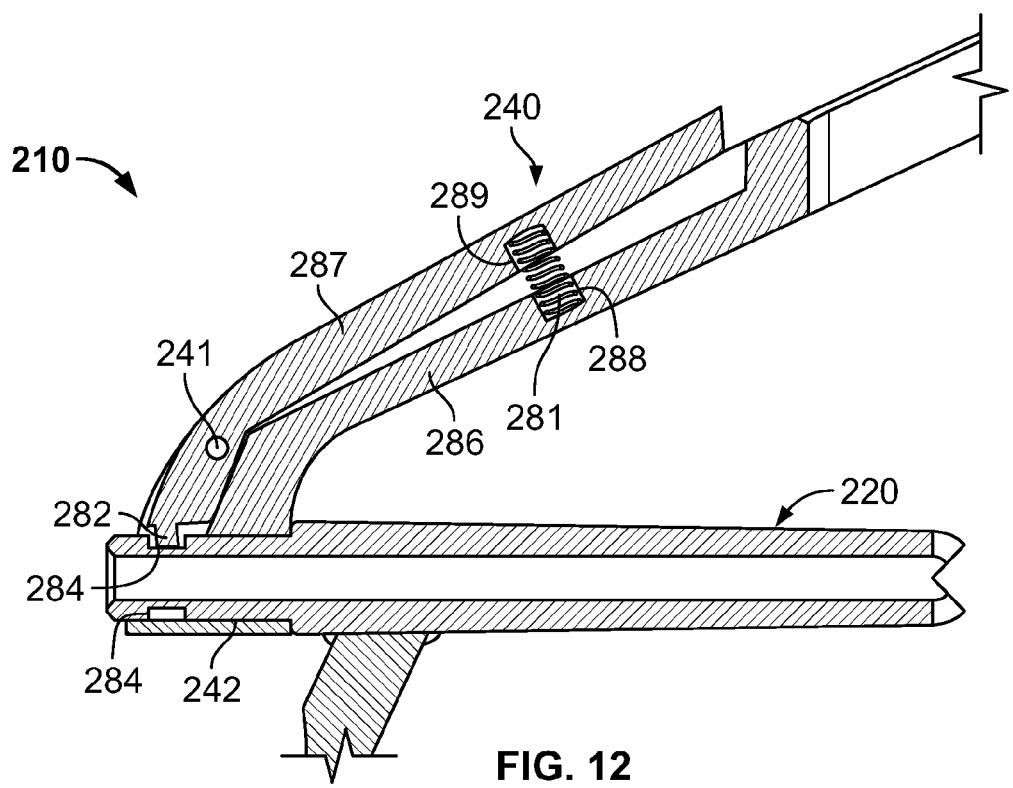
FIG. 12 is a cross-sectional view of a portion of an aiming device in accordance with another embodiment.

In the example shown in FIG. 12, aiming device 210 includes an assembly of sleeve 220 with arm 240. Arm 240 includes body 286 and lever 287 attached to each other by pin 241 extending from body 286 in a direction transverse to the longitudinal axis of sleeve 220 when the sleeve is received within aperture 242 of arm 240. Lever 287 pivots within a central plane passing through both sleeve 120 and arm 240 about pin 241 of arm 240.

Prong 282 extends from a proximal end of lever 287 such that when arm 240 is rotated to predetermined positions about the circumference of groove 185 of sleeve 120, as described with respect to aiming device 110, prong 282 extends into respective indentations 284 of sleeve 120 to lock arm 240 relative to sleeve 120. Depression of lever 287 causes prong 282 to move in a slight arc such that, when prong 282 is situated within any one of indentations 284 of sleeve 120, prong 282 exits from the respective indentation into which the prong is inserted. Once prong 282 exits the respective indentation 284, arm 240 is free to rotate about sleeve 120 so long as lever 287 is depressed.

Body 286 and lever 287 have aligned body groove 288 and lever groove 289, respectively, that are each distal to pin 241 of arm 240. Resilient element 281 extends between, and may be attached to, a base surface of each of body groove 288 and lever groove 289. As shown in FIG. 12, resilient element 281 may be, but is not limited to being, a coiled spring biased to provide a force to maintain separation of a portion of lever 287 distal to pin 241 from a portion of body 286 distal to pin 241. As shown, such separation corresponds to a biased default axial position of lever 287 as well as of prong 282 relative to groove 185 of sleeve 120. When lever 287 is in the default position, prong 282 axially aligns with indentations 284 such that prong 282 becomes inserted into one of indentations 284 upon rotation of arm 240 when prong 282 is not already so inserted.

Figure 13:
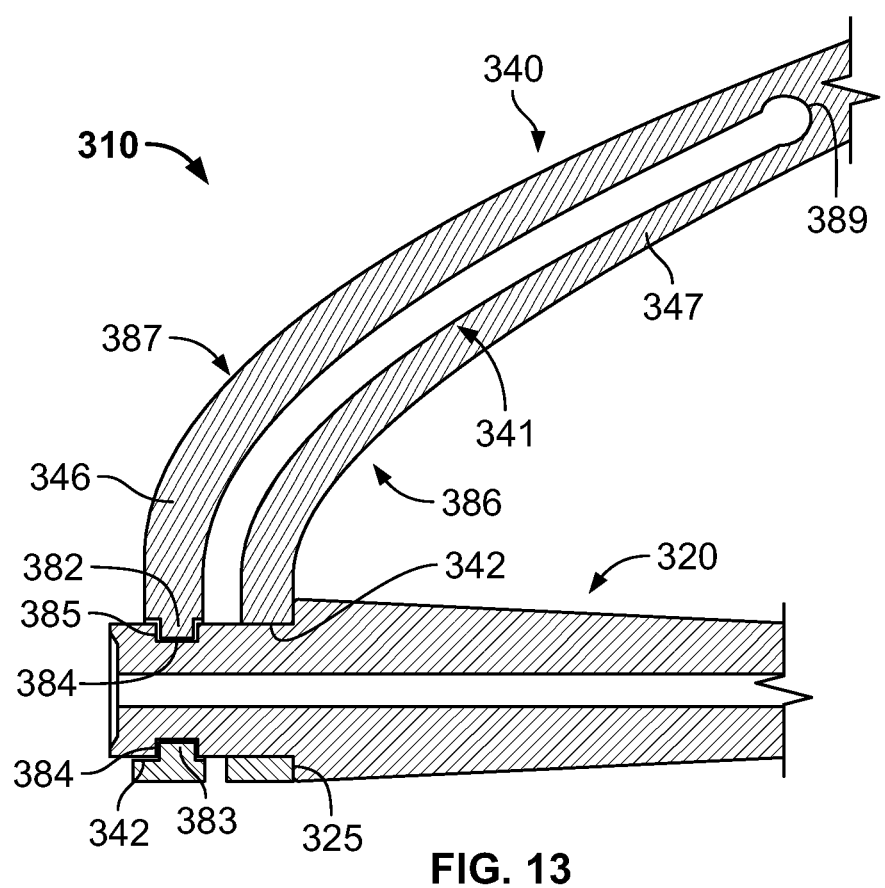
FIG. 13 is a cross-sectional view of a portion of an aiming device in accordance with another embodiment.

As shown in the arrangement of FIG. 13, aiming device 310 includes an assembly of sleeve 320 with arm 340. Sleeve 320 is substantially similar to sleeve 120 with the exception that sleeve 320 includes a series of indentations 384 in groove 385 extending around a circumference of the sleeve in which each indentation is diametrically opposed to another of the indentations. Arm 340 is substantially similar to arm 40 with the exception that central groove 341 extends from central section 347 of arm 340 and completely through proximal section 346, including across the diameter of aperture 342 of arm 340. In this manner, central groove 341 defines inner edges of distal and proximal forks 386, 387 of arm 340 and splits aperture 342 into two separated parts.

Proximal fork 386 of arm 340 includes upper prong 382 and opposing lower prong 383 which both extend into the portion of aperture 342 defined by proximal fork 387. In this manner, when arm 340 is rotated to predetermined positions about the circumference of groove 385 of sleeve 320, both upper prong 382 and lower prong 383 extend into respective opposing indentations 384 of sleeve 320 to lock arm 340 relative to sleeve 320.

Distal fork 386 abuts step 325 of sleeve 320 when sleeve 320 is fully received in aperture 342. In this manner, distal and proximal forks 386, 387 may be squeezed together such that proximal fork 387 and thus upper and lower prongs 382, 383 move in a slight arc to enable release of these prongs from any one of indentations 384 of sleeve 320 when so situated. In this configuration, arm 340 is free to rotate about sleeve 320. Central groove 341 includes notch 389, which as shown may be but is not limited to being a circular-shaped, on its distal end to provide stress relief from stresses that may otherwise be induced during movement of proximal fork 387 relative to distal fork 386.

A variation of aiming device 310 (not shown) combines sleeve 120 with an arm identical to arm 340 with the exception that the arm does not include lower prong 383. In such an arrangement, when upper prong 382 extends into indentations 184 of sleeve 120, the arm is locked relative to sleeve 120.

Figure 14A:
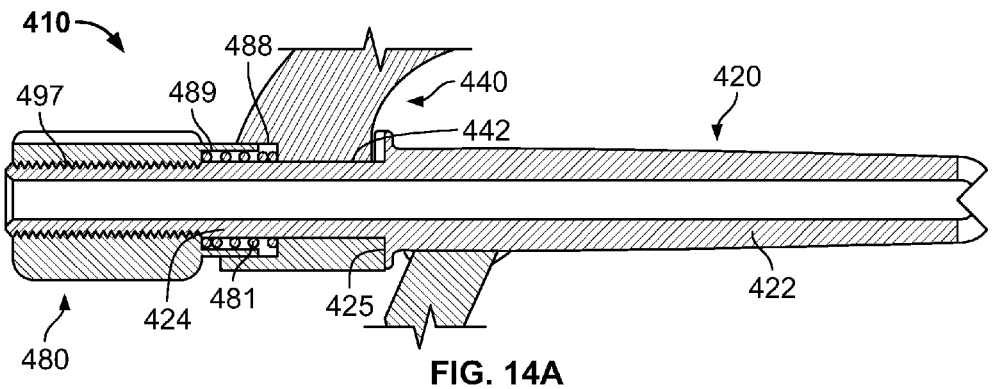
FIG. 14A is a cross-sectional view of a portion of an aiming device in accordance with another embodiment.
Figure 14B:
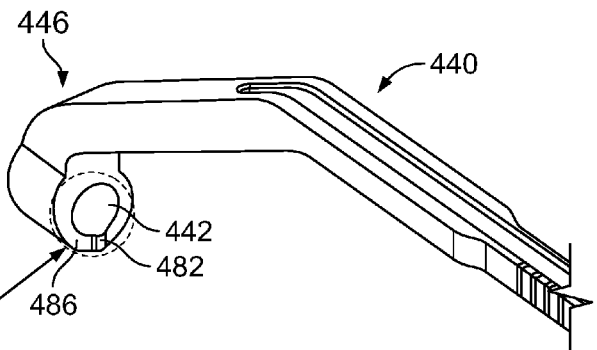
FIG. 14B is a perspective view of a portion of an arm of the aiming device of FIG. 14A.
Figure 14D:
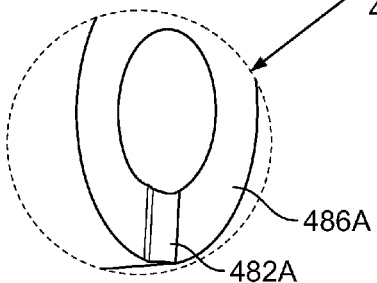
FIG. 14D is a perspective view of an alternative end of the arm of FIG. 14B.
Figure 14C:
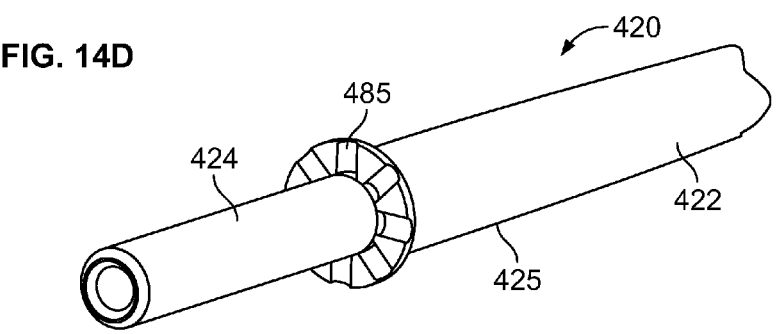
FIG. 14C is a perspective view of a sleeve of the aiming device of FIG. 14A.

In another arrangement shown in FIGS. 14A-14C, aiming device 410 includes an assembly of arm 440 held in axial position between sleeve 420 and retainer 480. As best shown in FIG. 14C, sleeve 420 includes step 425 defined by distal and proximal sections 422, 424 of sleeve 420. A plurality of grooves 485 extend radially from step 425. A corresponding proximally-facing surface 486 of proximal section 446 of arm 440 includes boss 482 that extends in a radial direction from aperture 442 of arm 440. Boss 482 is sized and positioned on proximally-facing surface 486 such that, when sleeve 420 is received within aperture 442 of arm 440, boss 482 fits within and substantially conforms to each of grooves 485 of sleeve 420 upon rotation of arm 440 about sleeve 420. Grooves 485 may be set at any location, although preferably the grooves may be set at equally spaced-apart intervals similar to the intervals discussed with respect to aiming device 110. In the example shown, longitudinal centerlines of grooves 485 are spaced apart 45 degrees from each other around the circumference of sleeve 420.

Aiming device 410 includes resilient element 481 that extends between arm 440 and retainer 480. As shown in FIG. 14A, resilient element 481 may be, but is not limited to being, a coiled spring biased to provide a force to maintain a separation between at least a portion of arm 440 and a portion of retainer 480. Retainer 480 may be attached, such as but not limited to by threading 497 as in the example shown or by way of a press-fit, to sleeve 420 such that retainer 480 does not translate relative to sleeve 420. In this manner, the combination of retainer 480 and resilient element 481 provides a force acting against arm 440 to hold arm 440 against sleeve 420. Such force acts to hold boss 482 within each of respective grooves 485 when so inserted. As further shown in FIG. 14A, resilient element 481 may extend between an end surface of each of arm groove 488 of arm 440 and retainer groove 489 of retainer 480 such that resilient element 481 is completely enclosed by a combination of the arm and the retainer.

Referring now to FIG. 14D, in a slightly altered arrangement of aiming device 410, proximally-facing surface 486 of proximal section 446 of arm 440 may be substituted with proximally-facing surface 486A having radial groove 482A in lieu of boss 482. In such an arrangement, step 425 of sleeve 420 corresponding to proximally-facing surface 486A may be substituted with a step having a plurality of bosses to form the sleeve (not shown). Such bosses may be spaced apart at the same intervals as grooves 485 of aiming device 410. In this manner, this altered arrangement of aiming device 410 operates in substantially the same manner as aiming device 410.

Figure 15A:
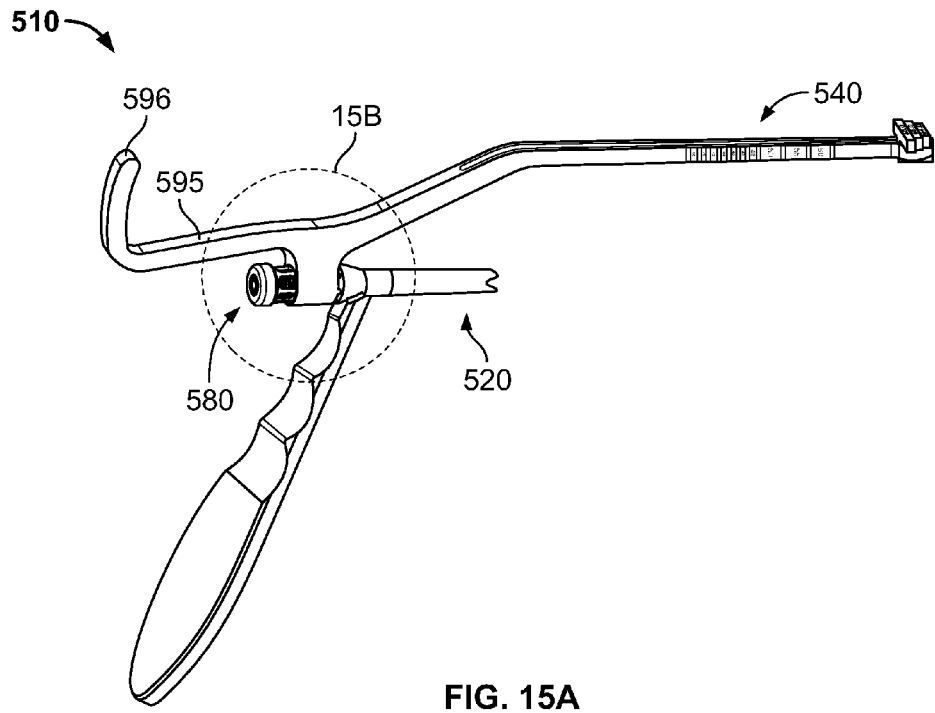
FIG. 15A is a perspective view of an aiming device in accordance with another embodiment.
Figure 15B:
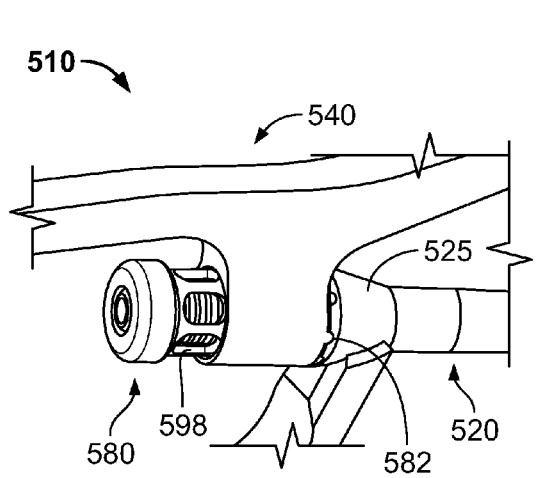
FIG. 15B is an enlarged perspective view of a portion of the aiming device of FIG. 15A.
Figure 15C:
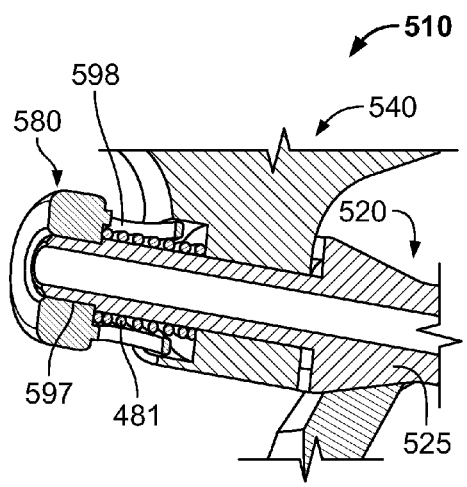
FIG. 15C is a cross-sectional view of the portion of the aiming device shown in FIG. 15B.

As shown in FIGS. 15A-15C, aiming device 510 is the same as aiming device 410 shown in FIGS. 14A-14C with certain exceptions. Aiming device 510 includes an assembly of arm 540 held in axial position between sleeve 520 and retainer 580. Sleeve 520 is the same as sleeve 420 with the exception that the sleeve is unthreaded on its proximal end and includes a thicker section 525 defining the step for abutment with arm 540.

In contrast to arm 440, arm 540 includes extension 595 extending proximally from the interface of arm 540 with sleeve 520. As shown, extension 595 may extend generally parallel to the longitudinal axis of sleeve 520. Arm 540 further includes trigger 596 extending from a proximal end of extension 595.

In lieu of retainer 480, aiming device 510 includes retainer 580 having an inner diameter 597 on its proximal end that is welded onto sleeve 520 to maintain the relative location of the retainer and the sleeve and avoid loss of spring tension, although in alternative arrangements, the retainer may be press-fit onto the sleeve or threaded for engagement with threads on the sleeve as in the case of other arrangements set forth herein. Retainer 580 includes windows 598 to provide access for cleaning the assembly of resilient element 481, sleeve 520, and retainer 580.

Aiming device 510 operates in substantially the same manner as aiming device 410 with the exception that arm 540 may be pulled at trigger 596 to compress resilient element 481 to allow for rotation of arm 540, and thus boss 582 of arm 540 extending in a distal direction, about sleeve 520.

Figure 16A:
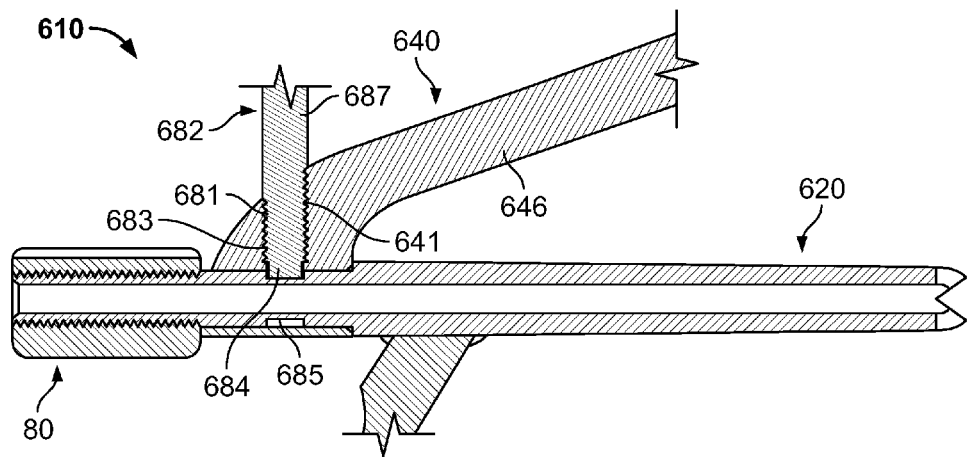
FIG. 16A is a cross-sectional view of a portion of an aiming device in accordance with another embodiment.
Figure 16B:
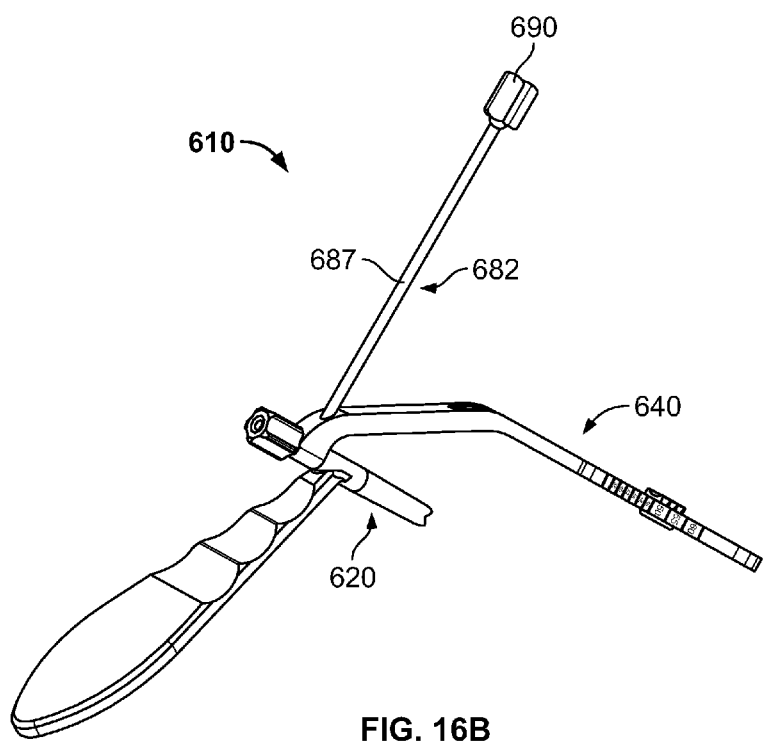
FIG. 16B is a perspective view of the aiming device of FIG. 16A.

In the arrangement shown in FIGS. 16A and 16B, aiming device 610 includes sleeve 620 and arm 640. Referring to FIG. 16A, sleeve 620 includes groove 685 extending around its circumference. Arm 640 includes bore 641 having threads 681 extending through its proximal section 646 in a direction that is transverse to a longitudinal axis of sleeve 620 when arm 640 is assembled with sleeve 620. Elongated screw device 682 includes threads 683 for engagement with threads 681 of arm 640 such that the screw device extends and is maintained in an orientation transverse, and preferably substantially perpendicular to, sleeve 620. When in threaded engagement with arm 640, screw device 682 may be easily removed from engagement with bore 641. As shown, screw device 682 has a sufficiently long shaft 687 such that insertion end 684 of the screw device may be inserted into groove 685 while a majority of the screw device protrudes from bore 641.

On an end of screw device 682 opposite insertion end 684 of the screw device is attached knob 690, as shown in FIG. 16B. Knob 690 has a greater outside perimeter than shaft 687 to aid in reducing the force necessary to provide sufficient torque to rotate screw device 682. When tightened to a sufficient torque, which may be in the range of 0.1 N·m to 1 N·m but which may be user dependent, arm 640 may be locked by screw device 682 in rotational position relative to sleeve 620.

Retainer 80 may be attached to sleeve 620 in the same manner as retainer 80 attaches to sleeve 20 of aiming device 10. In this manner, when sleeve 620 is received in arm 640 and retainer 80 is attached to sleeve 620 and tightened against arm 640, arm 640 may be locked in axial position relative to sleeve 620. Moreover, tightening of retainer 80 against arm 640 creates friction against arm 640 which provides additional resistance to rotational movement of arm 640 relative to sleeve 620.

Figure 17:
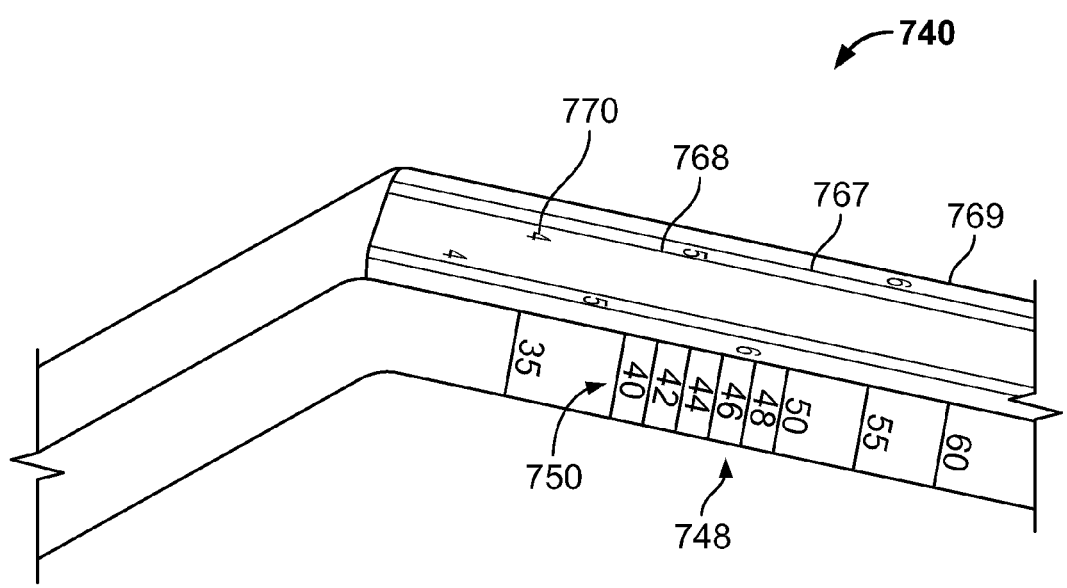
FIG. 17 is a perspective view of a section of an arm of an aiming device in accordance with another embodiment.

Referring now to FIG. 17, an alternative arrangement of aiming device 10 may include arm 740, as shown, and may not include a block, such as block 60. Arm 740 may not include a slot, such as slot 45, extending along distal end 748 of the arm. Arm 740 may include length indicia 750 along sides of distal end 748 and width indicia 770 extending along a top surface intersecting the sides of distal end 748.

Parallel opposing width boundaries 767, 768, 769 extending along the top surface of distal end 748 correspond to a specific width indicium of width indicia 770. In the example shown, opposing inner width boundaries 768 correspond to a 4.0 mm width, opposing outer width boundaries 769 correspond to a 6.0 mm width, and opposing middle width boundaries 767 situated between the inner width boundaries and the outer width boundaries correspond to a 5.0 mm width. As shown, outer width boundaries 769 may extend along the opposing edges of distal end 748 of arm 740.

A portion or, as in the example shown, all of arm 740 may be made of a radiolucent material, such as but not limited to plastics including polyethylene and propylene, with the exception of length indicia 750, width indicia 770, width boundaries 767, 768, and 769, which may be made of a radiopaque material, such as but not limited to aluminum, stainless steel, and titanium. Arm 740, along with any other arrangements of the arm set forth herein, is intended to be rigid to avoid flexure that might cause inaccurate measurements to be taken.

Length indicia 750, width indicia 770, width boundaries 767, 768, and 769 may be visible during radiographic viewing of arm 740 to aid in determining appropriate dimensions of objects, such as bone. In one example, arm 740 may be used in conjunction with a sleeve of an aiming device, such as sleeve 20 of aiming device 10, to ascertain appropriate dimensions for the implant as well as for appropriate positioning of the implant in a particular bone or in portions of particular bones.

In alternative arrangements of screw 500, the screw may have a solid core. In some arrangements, the screw may have a conical tip. In some arrangements, the screw may not have reverse cutting flutes. In some arrangements, the screw may not have self-tapping grooves.

In an alternative arrangement of aiming device 10, any of the width and length indicia, such as length indicia 50 and width indicia 70, may be but are not limited to being engraved, chemically etched, and laser etched.

In another alternative arrangement of aiming device 10, the arm may be made out of a radiolucent material, such as but not limited to a polymer or other plastic. In such arrangements, a limited number of radiopaque markers, which may be but are not limited to being made of metallic material may be incorporated into the radiolucent material to preserve visibility of the overall arm position on X-rays or fluoroscopic imaging.

In another alternative arrangement of aiming device 10, when the arm is made out of a radiolucent material, any of the width and length indicia, such as length indicia 50 and width indicia 70, may be made out of a radiopaque material to form radiopaque markers. In another alternative arrangement, when the arm is made out of a radiopaque material, such as aiming device 10 described herein, any of the width and length indicia may be made out of a radiolucent material to form radiolucent markers. In either of these alternatives, the width and length indicia may be prominent during radiographic viewing such that they may be readable during such viewing.

In another alternative arrangement of aiming device 10, the device may be provided with multiple arms, which may be swiveling, to provide radiographic or direct visualization in multiple viewing planes. In another alternative arrangement of aiming device 10, the arm, or in some arrangements multiple arms, may be directly mounted onto a driving instrument, e.g., a power tool for turning the drill. In such an arrangement, the sleeve, and in some instances the retainer, may be unnecessary.

In another alternative arrangement of aiming device 10, the block may have fewer or greater delineations and indicia than block 60.

In another alternative arrangement of aiming device 10, the block may be but is not limited to being an open-ended hollow shell such that the block may be attached to the arm by surrounding the perimeter of the arm. In some such arrangements, the inner perimeter of the block may be slightly smaller than an outer perimeter of the arm. In this manner, the block may be held in place when external forces, such as those applied by a user of the aiming device, are applied. In some such arrangements, the block may have an opening on one or both of its sides to allow for viewing of the length indicia.

In another set of alternative arrangements of aiming device 10, one of the block and arm may have a male cross-section along its length for mating with the other of the block and the arm which has a female connection to form a dovetail connection between the block and the arm.

In an alternative arrangement of aiming device 10, the arm may be fully fixed to the sleeve by any known fixation methods, such as welding or fastening using screws or other fasteners. In some such arrangements, the retainer and threading on the proximal section of the sleeve may be unnecessary. In another alternative arrangement, a friction member, such as but not limited to an O-ring, may be interposed between the sleeve and the arm. In this manner, the friction member may provide sufficient friction to hold the arm in a fixed position and orientation relative to the sleeve when no external forces, such as those that may be provided by a user of the aiming device, are applied.

In an alternative arrangement of aiming device 10, the retainer may be press-fit onto the proximal-most end of the proximal section of the sleeve to compress the proximal section of the arm against the step. In this manner, the arm may be fixed in relative axial position to the sleeve. Furthermore, when the arm compressed sufficiently between the retainer and the step of the sleeve, the arm may be fixed in relative angular orientation to the sleeve. In another alternative, the arm may be fixed, such as by but not limited to being by welding, in relative position to the sleeve.

In some alternative arrangements of a kit including an aiming device such as aiming device 10, each drill of the kit may have a corresponding drill protecting sleeve having an inner diameter of the sleeve that is the same or substantially the same as the outer diameter of the respective drill. Similarly, in some alternative arrangements of a kit including an aiming device such as aiming device 10, each tap of the kit may have a corresponding tap protecting sleeve having an inner diameter of the sleeve that is the same or substantially the same as the outer diameter of the respective tap.

It is to be understood that the disclosure set forth herein includes all possible combinations of the particular features set forth above, whether specifically disclosed herein or not. For example, where a particular feature is disclosed in the context of a particular aspect, arrangement, configuration, or embodiment, that feature can also be used, to the extent possible, in combination with and/or in the context of other particular aspects, arrangements, configurations, and embodiments of the invention, and in the invention generally.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the claims below. Moreover, the foregoing disclosure should be taken by way of illustration rather than by way of limitation as the present invention is defined by the claims set forth below.

The invention claimed is:

1. A device for assisting in the positioning and sizing of an implant comprising:
   an elongate member having a straight portion defining a longitudinal axis and including a surface providing a predetermined datum and length indicia for measuring a first distance from the predetermined datum of the elongate member, the predetermined datum and the length indicia being located at axial locations along an axis parallel to the longitudinal axis defined by the straight portion of the elongate member;

a cannulated sleeve defining a longitudinal axis, wherein the elongate member is in the form of an arm and includes a front portion and a rear portion opposite the front portion, the rear portion of the elongate member being attached to and extending from the sleeve, and the front portion of the elongate member extending in a direction substantially parallel to the longitudinal axis defined by the sleeve and including the length indicia; and a block attached to and movable along the straight portion of the elongate member, the block including width indicia for measuring a second distance in a direction transverse to the first distance.

2. The device of claim 1, wherein the block is movable to each of the axial locations along the elongate member.

3. The device of claim 1, wherein the sleeve has at least a first section defined by a first diameter and a second section defined by a second diameter, the first diameter being less than the second diameter, and wherein the elongate member includes an aperture for receiving the first diameter of the sleeve.

4. The device of claim 1, wherein the elongate member is rotatable about the sleeve such that either one or both of the length and the width indicia are viewable in a plurality of angular positions of the arm.

5. The device of claim 1, further comprising:
a retainer holding the sleeve to the elongate member.

6. The device of claim 5, further comprising:
a resilient element between a first surface of the elongate member and a surface of the retainer, the retainer being fixedly attached to the sleeve,
wherein the elongate member is rotatable about the sleeve,
wherein the sleeve includes a plurality of sleeve indentations or a plurality of sleeve bosses around a circumference thereof,
wherein the elongate member includes either an elongate member boss for receipt in each of the plurality of sleeve indentations or an elongate member indentation for receipt of each of the sleeve bosses, and wherein when the elongate member boss is received in one of the plurality of sleeve indentations or the elongate member indentation is in receipt of one of the sleeve bosses, the resilient element provides an axial force against the elongate member to hold a second surface of the elongate member opposite the first surface against a surface of the sleeve such that a greater rotational force is required to rotate the elongate member about the sleeve than when the elongate member includes the elongate member boss and the elongate member boss is not received in one of the plurality of sleeve indentations or when the elongate member includes the elongate member indentation and the elongate member indentation is not in receipt of one of the sleeve bosses.

7. The device of claim 6, wherein the first surface of the elongate member is within a groove of the elongate member and the surface of the retainer is within a groove of the retainer.

8. The device of claim 6, wherein a trigger extends from the elongate member, wherein when the trigger is pulled from a first position to a second position, the elongate member compresses the resilient element such that the second surface of the elongate member is held away from the surface of the sleeve to allow for rotation of the elongate member about the sleeve.

9. The device of claim 1, wherein the elongate member defines a slot.

10. The device of claim 9, wherein a portion of the block is received in the slot of the elongate member and has grooves on opposite sides for receiving a portion of the elongate member such that when the block moves along the slot, the block is maintained within the slot.

11. The device of claim 1, wherein at least a portion of at least one of the elongate member and the block is at least partially radiopaque or radiolucent during radiographic viewing.

12. The device of claim 1, at least one of the length indicia being alignable with a position for insertion of a portion of the implant, wherein the block is moveable to an axial location of the elongate member aligned with the position to which the portion of an implant is to be inserted.

13. A system for assisting in the positioning and sizing of an implant comprising:
the device of claim 1, wherein the elongate member defines a slot; and
a guide wire extending through the sleeve of the device, wherein an end of the guide wire is visible through the slot of the elongate member.

14. The system of claim 13, wherein the elongate member is radiographically viewable, and wherein an end of the guide wire is radiographically viewable through the slot of the elongate member.

15. The device of claim 1, wherein the elongate member is rotatable about the sleeve, wherein the sleeve includes a plurality of indentations around a circumference thereof, wherein the elongate member includes a body and an insertion element moveable relative to the body, and wherein when the insertion element is in alignment with one of the indentations, a greater force is required to rotate the elongate member about the sleeve than when the insertion element does not extend into any of the indentations.

16. The device of claim 15, wherein the insertion element of the elongate member and the indentations of the sleeve form a detent assembly.

17. The device of claim 16, wherein the detent assembly includes a resilient element and a ball, the resilient element being located in a bore of the body of the elongate member and wherein when the insertion element is in alignment with one of the indentations, the ball extends into the aligned indentation.

18. The device of claim 15, wherein the insertion element is a lever pivotable about the body, wherein when the lever is in a first position relative to the body, the lever extends into the aligned indentation, and when the lever is in a second position relative to the body, the insertion element does not extend into the aligned indentation.

19. The device of claim 18, wherein a resilient member extends between a first surface of the body of the elongate member and a second surface of the lever of the elongate member, and wherein the resilient member biases the lever in the first position thereof.

20. The device of claim 15, wherein the insertion element and the body are spaced apart cantilevers extending from a main body of the elongate member.

21. The device of claim 1, wherein the sleeve includes a groove around a circumference thereof and the elongate member includes a body and an insertion element moveable relative to the body in order to contact a base surface of the sleeve including the groove, wherein when the insertion element is in contact with the base surface, a greater force is required to rotate the elongate member about the sleeve than when the insertion element is not in contact with the base surface.

22. The device of claim 21, wherein the insertion element is an elongated screw device.

23. A device for assisting in the positioning and sizing of an implant comprising:
   an elongate member having a straight portion defining a longitudinal axis and including a surface providing a predetermined datum and length indicia for measuring a first distance from the predetermined datum of the elongate member, the predetermined datum and the length indicia being located at axial locations along an axis parallel to the longitudinal axis defined by the straight portion of the elongate member; and
   a block attached to and movable along the straight portion of the elongate member, wherein the block includes width indicia for measuring a second distance in a direction transverse to the first distance, the block further including a plurality of sections, each section defining a corresponding measurement surface having a different width than the measurement surfaces of the other sections of the plurality of sections, each different width defining a respective width index of the block.

24. A device for assisting in the positioning and sizing of an implant comprising:
   an elongate member having a straight portion defining a longitudinal axis and a slot, the elongate member including a surface providing a predetermined datum and length indicia for measuring a first distance from the predetermined datum of the elongate member, the predetermined datum and the length indicia being located at axial locations along an axis parallel to the longitudinal axis defined by the straight portion of the elongate member; and
   a block attached to and movable along the straight portion of the elongate member, the block including width indicia for measuring a second distance in a direction transverse to the first distance, wherein a portion of the block is received in the slot of the elongate member.

25. The device of claim 24, wherein the portion of the block has grooves on opposite sides for receiving a portion of the elongate member such that when the block moves along the slot, the block is maintained within the slot.

* * * * *